United States Patent [19]
Cooper et al.

[11] Patent Number: 6,166,206
[45] Date of Patent: Dec. 26, 2000

[54] PYRROLO[3,4-D]PYRIMIDINONE DERIVATIVES AND THEIR USE AS MEDICAMENTS

[75] Inventors: Martin E Cooper; David R Cheshire; David K Donald; Mark Furber; Matthew W. D Perry; Richard P Harrison; Nicholas P Tomkinsson, all of Leics, United Kingdom

[73] Assignee: AstraZeneca UK Limited, London, United Kingdom

[21] Appl. No.: 09/506,090

[22] Filed: Feb. 17, 2000

Related U.S. Application Data

[63] Continuation of application No. 09/011,780, filed as application No. PCT/SE97/02157, Dec. 18, 1997, Pat. No. 6,046,204.

[30] Foreign Application Priority Data

Dec. 21, 1996 [GB] United Kingdom .................... 9626643

[51] Int. Cl.$^7$ .................................................. C07D 487/04
[52] U.S. Cl. ............................................................... 544/280
[58] Field of Search .............................................. 544/280

[56] References Cited

FOREIGN PATENT DOCUMENTS

93/04047  3/1993  WIPO .
96/17610  6/1996  WIPO .

OTHER PUBLICATIONS

Michne et al, "Novel Inhibitors of the Nuclear Factor of Activated T Cells (NFAT)–Mediated . . . ," J. Med. Chem., vol. 38, pp. 2557–2569 (1995).

Noguchi et al, "A Facile Preparation of 7–(Substituted amino)–6H–pyrrolo[3,4–d]–pyrimidine Derivatives[1]," Bull. Chem. Soc. Jpn., vol. 62, pp. 3043–3045 (1989).

Hirota et al, "Pyrimidine Derivatives and Related Compounds. XXXIII.[1)] Reactions of . . . ," Chem. Pharm. Bull., vol. 29, No. 6, pp. 1525–1532 (1981).

Senda et al, "A Facile Synthesis of Pyrrolo[3,4–d]pyrimidines and Pyrimido[4,5–d]pyridazines," Communications, "Synthesis," pp. 463–465 (1978).

Baines et al, "Functional Characterization of Novel IL–2 Transcriptional Inhibitors," The Journal of Immunology, vol. 154, pp. 3667–3677 (1995).

*Primary Examiner*—John M. Ford
*Attorney, Agent, or Firm*—Nixon & Vanderhye

[57] ABSTRACT

The invention provides certain novel 5-substituted pyrrolo [3,4-d]pyrimidine-2,4-diones, processes for their preparation, pharmaceutical compositions containing them, a process for preparing the pharmaceutical compositions, and methods of treatment involving their use.

1 Claim, No Drawings

PYRROLO[3,4-D]PYRIMIDINONE DERIVATIVES AND THEIR USE AS MEDICAMENTS

This is a continuation of application Ser. No. 09/011,780, filed Feb. 24, 1998 now U.S. Pat. No. 6,046,204 allowed, the entire content of which is hereby incorporated by reference in this application which is a 371 of PCT/SE97/02157, filed Dec. 18, 1997.

The present invention provides certain novel 5-substituted pyrrolo[3,4-d]-pyrimidine-2,4-diones, processes for their preparation, pharmaceutical compositions containing them, a process for preparing the pharmaceutical compositions, and methods of treatment involving their use.

T-cells play an important role in the immune response, however in autoimmune disease T-cells are activated against particular tissues, e.g. causing the inflammation associated with rheumatoid arthritis. Interleukin-2(IL-2) is an essential autocrine growth factor for T-cells and hence inhibition of IL-2 transcription is beneficial in the modulation of autoimmune disease. Formation of a transcriptional complex of the protein nuclear factor of activated T-cells-1 (NFAT-1) on the IL-2 promoter is essential for IL-2 transcription. NFAT-1 mediated transcription has therefore been proposed as appropriate molecular target for immunomodulation, Y. Baine et al., *J. Immunol.*, 1995, 154, 3667–3677.

W. F. Michne et al., in *J. Med. Chem.* (1995) 38,2557–2569 disclose a number of quinazoline-2,4-diones and pyrrolo[3,4-d]pyrimidine-2,4-diones which inhibit transcription regulated by the DNA region bound by the NFAT-1 protein.

WO 96/17610 discloses the use of compounds of the following general formula and their salts as anti-ischaemic agents,

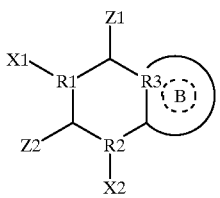

wherein R1, R2 and R3 which may be the same or different are N or CH; X1 and X2 which may be the same or different are hydrogen, hydroxy or an optionally substituted alkyl, alkenyl, alkynyl, cycloalkyl, aryl or heterocyclyl group and Z1 and Z2 which may be the same or different are hydrogen, hydroxy, keto or an optionally substituted alkyl, alkenyl, alkynyl, cycloalkyl, aryl or heterocyclyl group or one of Z1 and X1 and Z2 and X2 form the second bond of a double bond at the 1,6 or 2,3 positions, with the proviso that at least one of the groupings R1Z1X1, R2Z2X2 and R1X1Z2 form a hydroxamate moiety (—N(OH)C(=O)—) in which R1 and/or R2 is N, Z1 and/or Z2 is =O and X1 and/or X2 is OH or R1 is N, Z2 is =O and X1 is OH and B is a 5- or 6-membered ring of formula

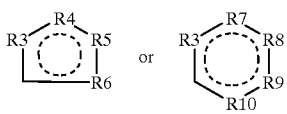

in which R4, R5, R6, R7, R8, R9 and R10 which may be the same or different are CH or N with the proviso that ring B cannot contain more than 3 ring members which are nitrogen and the ring B may optionally be substituted by one or more of hydroxy, keto and an optionally substituted alkyl, alkenyl, alkynyl, cycloalkyl, aryl or heterocyclyl group. Preferred compounds of WO 96/17610 include those compounds in which the ring B contains no substituent groups.

In accordance with the present invention, there is provided a compound according to the general formula:

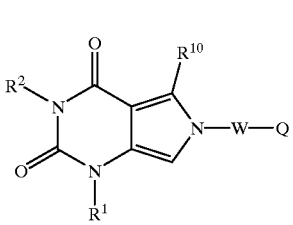

(I)

wherein

W represents —$CH_2$— or a bond; Q represents $Ar^1$ or $Ar^2$; in the case where W represents —$CH_2$—, Q represents an aryl group $Ar^1$ wherein $Ar^1$ represents naphthyl, phenyl, quinolyl, isoquinolyl, indolyl, benzofuranyl or benzothienyl; in the case where W represents a bond, Q represents an aryl group $Ar^2$ wherein $Ar^2$ represents acenaphthenyl, fluorenyl or indanyl; wherein the ring systems which $Ar^1$ and $Ar^2$ represent may all be optionally substituted by one or more substituents selected from $C_{1-4}$ alkyl, $C_{1-4}$ alkoxy, halogen, or trifluoromethyl; $R^{10}$ represents X—$(A)_p$—Y; X represents $S(O)_n$, C≡C, $(CH_2)_2$, CH=CH or $CH_2CH$=CH; n represents 0, 1 or 2; A represents $C_{1-6}$ alkylene; p is 0 or 1; Y represents CN, $OR^{11}$, $CO_2R^{12}$, $CONR^{13}R^{14}$, $NR^{15}R^{16}$, $NHSO_2R^{17}$, $NHCOR^{18}$ or an optionally substituted aryl or heteroaryl group, provided that when X represents $S(O)_n$ and Y is other than an optionally substituted aryl or heteroaryl group, then p is 1 and also provided that when X represents $S(O)_n$, p is 1 and Y represents OH, then n is not 0; $R^{13}$ and $R^{14}$ independently represent H, $C_{1-5}$ alkyl or phenyl, which latter group may be substituted by one or more substituents selected from $C_{1-4}$ alkyl, $C_{1-4}$ alkoxy, halogen, or $CO_2R^{21}$; and $R^1$, $R^2$, $R^{11}$, $R^{12}$, $R^{15}$, $R^{16}$, $R^{17}$, $R^{18}$ and $R^{21}$ independently represent H or $C_{1-5}$ alkyl; or a pharmaceutically acceptable derivative thereof.

In the present specification, unless otherwise indicated, an alkyl substituent or alkyl moiety in an alkoxy, alkoxycarbonyl, alkylsulphonamido, (di)alkylamido, (di) alkylamino or acylamino substituent group may be linear or branched.

When W in formula (I) represents —$CH_2$—, then Q represents an aryl group $Ar^1$ wherein $Ar^1$ preferably represents a naphthyl or phenyl group, especially a naphthyl group, which aryl group may be optionally substituted by one or more, preferably one to four, particularly one or two, substituents selected from $C_{1-4}$ alkyl, e.g., methyl or ethyl, $C_{1-4}$ alkoxy, e.g. methoxy or ethoxy, halogen, e.g. fluorine, chlorine or bromine, or trifluoromethyl. $Ar^1$ is preferably an unsubstituted naphthyl group.

When W in formula (I) represents a bond, then Q represents an aryl group $Ar^2$ wherein $Ar^2$ preferably represents an indanyl group, which may be optionally substituted by one or more, preferably one to four, particularly one or two, substituents selected from $C_{1-4}$ alkyl, e.g. methyl or ethyl, $C_{1-4}$ alkoxy, e.g. methoxy or ethoxy, halogen, e.g. fluorine, chlorine or bromine, or trifluoromethyl. $Ar^2$ is preferably an unsubstituted indanyl group.

Preferably, X represents $S(O)_n$ wherein n is 0, 1 or 2, C≡C, $(CH_2)_2$ or $CH_2CH$=CH. Particularly advantageous compounds of formula (I) are those in which X represents $S(O)_n$ wherein n is 0, 1 or 2.

When p is 1, A preferably represents $C_{1-4}$ alkylene, more preferably $CH_2$, $(CH_2)_2$ or $(CH_2)_3$.

Each of groups $R^1$, $R^2$, $R^{11}$, $R^{12}$, $R^{15}$, $R^{16}$, $R^{17}$, $R^{18}$ and $R^{21}$ preferably represents H or a $C_{1-4}$ alkyl group. $R^1$ is most preferably a cyclic or branched $C_{3-4}$ alkyl group, e.g., a 1-methylethyl or 2-methylpropyl group, and $R^2$ is most preferably a methyl group.

Each of groups $R^{13}$ and $R^{14}$ preferably represents H, $C_{1-3}$ alkyl or phenyl, which latter group may be substituted by one or more, e.g. one to four, substituents selected from $C_{1-4}$ alkyl, e.g., methyl or ethyl, $C_{1-4}$ alkoxy, e.g., methoxy or ethoxy, halogen, e.g. fluorine, chlorine or bromine, or $CO_2R^{21}$.

More preferably, each of groups $R^{13}$ and $R^{14}$ represents H, $C_{1-3}$ alkyl or phenyl, which latter group may be substituted by one or two substituents selected from $C_{1-4}$ alkyl, $C_{1-4}$ alkoxy, halogen, or $CO_2R^{21}$.

Most preferably, each of groups $R^{13}$ and $R^{14}$ represents H, $C_{1-3}$ alkyl or phenyl, especially H.

The group Y may represent an optionally substituted aryl or heteroaryl group. Preferably p is 0 when Y represents an optionally substituted aryl or heteroaryl group. Examples of aryl and heteroaryl groups include phenyl, furyl, imidazolyl, pyrazinyl, pyrazolyl, pyridazinyl, pyridyl, pyrimidinyl, pyrrolyl, tetrazolyl and thienyl groups. The groups phenyl, 2-pyridyl, 4-pyridyl and 5-tetrazolyl are most preferred. Examples of substituents that may be present in the aryl or heteroaryl group include $C_{1-4}$ alkyl, e.g. methyl or ethyl, $C_{1-4}$ alkoxy, e.g. methoxy or ethoxy, halogen, e.g. fluorine, chlorine or bromine, hydroxyl and trifluoromethyl. One or more, e.g. 1,2,3 or 4, substituent groups may be present but preferably only one substituent group is present.

A preferred subset of compounds of formula (I) is one in which W represents —$CH_2$— or a bond; Q represents $Ar^1$ or $Ar^2$; in the case where W represents —$CH_2$—, Q represents an aryl group $Ar^1$ wherein $Ar^1$ represents naphthyl or phenyl; in the case where W represents a bond. Q represents an aryl group $Ar^2$ wherein $Ar^2$ represents indanyl; wherein the ring systems which $Ar^1$ and $Ar^2$ represent may all be optionally substituted by one or more, e.g. one, two, three or four, substituents selected from $C_{1-4}$ alkyl, $C_{1-4}$ alkoxy, halogen, or trifluoromethyl; $R^{10}$ represents X—$(A)_p$—Y; X represents $S(O)_n$, C≡C, $(CH_2)_2$ or $CH_2CH$=CH; n represents 0, 1 or 2; A represents $C_{1-6}$ alkylene; p is 0 or 1; Y represents CN, $OR^{11}$, $CO_2R^{12}$, $CONR^{13}R^{14}$, $NR^{15}R^{16}$ or an optionally substituted phenyl, pyridyl or tetrazolyl group, provided that when X represents $S(O)_n$ and Y is other than an optionally substituted aryl or heteroaryl group, then p is 1 and also provided that when X represents $S(O)_n$, p is 1 and Y represents OH, then n is not 0; $R^{13}$ and $R^{14}$ independently represent H, $C_{1-5}$ alkyl or phenyl, which latter group may be substituted by one or more, e.g. one, two, three or four, substituents selected from $C_{1-4}$ alkyl, $C_{1-4}$ alkoxy, halogen, or $CO_2R^{21}$; and $R^1$, $R^2$, $R^{11}$, $R^{12}$, $R^{15}$, $R^{16}$ and $R^{21}$ independently represent H or $C_{1-5}$ alkyl.

An especially preferred subset of compounds of formula (I) is one in which W represents —$CH_2$— or a bond; Q represents $Ar^1$ or $Ar^2$; in the case where W represents —$CH_2$—; Q represents an aryl group $Ar^1$ wherein $Ar^1$ represents naphthyl; in the case where W represents a bond, Q represents an aryl group $Ar^2$ wherein $Ar^2$ represents indanyl; $R^{10}$ represents X—$(A)_p$—Y; X represents $S(O)_n$, C≡C, $(CH_2)_2$ or $CH_2CH$=CH; n represents 0, 1 or 2; A represents $C_{1-3}$ alkylene; p is 0 or 1; Y represents CN, $OR^{11}$, $CO_2R^{12}$, $CONR^{13}R^{14}$, $NR^{15}R^{16}$ or a phenyl, pyridyl or tetrazolyl group optionally substituted by a hydroxyl or methoxy group, provided that when X represents $S(O)_n$ and Y is other than an optionally substituted aryl or heteroaryl group, then p is 1 and also provided that when X represents $S(O)_n$, p is 1 and Y represents OH, then n is not 0; $R^{13}$ and $R^{14}$ independently represent H; and $R^1$, $R^2$, $R^{11}$, $R^{12}$, $R^{15}$ and $R^{16}$ independently represent H or $C_{1-4}$ alkyl.

Specific examples of preferred compounds of formula (I) are:

(i) 5-[(3-hydroxypropyl)sulphinyl]-3-methyl-1-(2-methylpropyl)-6-(1-naphthalenylmethyl)-1H-pyrrolo[3,4-d]pyrimidine-2,4(3H,6H)-dione;

(ii) 5-[(3-hydroxypropyl)sulphonyl]-3-methyl-1-(2-methylpropyl)-6-(1-naphthalenylmethyl)-1H-pyrrolo[3,4-d]pyrimidine-2,4(3H,6H)-dione;

(iii) methyl-4-[(2,3,4,6-tetrahydro-3-methyl-1-(2-methylpropyl)-6-(1-naphthalenylmethyl)-2,4dioxo-1H-pyrrolo[3,4-d]pyrimidin-5-yl)thio]butanoate;

(iv) 5-[(3-methoxypropyl)thio]-3-methyl-1-(2-methylpropyl)-6-(1-naphthalenylmethyl)-1H-pyrrolo[3,4-d]pyrimidine-2,4(3H,6H)-dione;

(v) 5-[(2-hydroxyethyl)sulphinyl]-3-methyl-1-(2-methylpropyl)-6-(1-naphthalenylmethyl)-1H-pyrrolo[3,4-d]pyrimidine-2,4(3H,6H)-dione;

(vi) 4-[(2,3,4,6-tetrahydro-3-methyl-1-(2-methylpropyl)-6-(1-naphthalenylmethyl)-2,4dioxo-1H-pyrrolo[3,4-d]pyrimidin-5-yl)thio]butanoic acid;

(vii) 4-[(2,3,4,6-tetrahydro-3-methyl-1-(2-methylpropyl)-6-(1-naphthalenylmethyl)-2,4dioxo-1H-pyrrolo[3,4-d]pyrimidin-5-yl)thio]butanoic acid, sodium salt;

(viii) 5-[(2-dimethylaminoethyl)thio]-3-methyl-1-(2-methylpropyl)-6-(1-naphthalenylmethyl)-1H-pyrrolo[3,4-d]pyrimidine-2,4(3H,6H)-dione;

(ix) 6-(2,3-dihydro-1H-inden-2-yl)-5-[(3-hydroxypropyl)sulphinyl]-3-methyl-1-(1-methylethyl)-1H-pyrrolo[3,4-d]pyrimidine-2,4(3H,6H)-dione;

(x) 6-(2,3-dihydro-1H-inden-2-yl)-5-[(3-hydroxypropyl)sulphonyl]-3-methyl-1-(1-methylethyl)-1H-pyrrolo[3,4-d]pyrimidine-2,4(3H,6H)-dione;

(xi) 5-[(3-hydroxypropyl)sulphinyl]-3-methyl-1-(1-methylethyl)-6-(1-naphthalenylmethyl)-1H-pyrrolo[3,4-d]pyrimidine-2,4(3H,6H)-dione;

(xii) 4-[(2,3,4,6-tetrahydro-3-methyl-1-(2-methylpropyl)-6-(1-naphthalenylmethyl)-2,4dioxo-1H-pyrrolo[3,4-d]pyrimidin-5-yl)thio]butanamide;

(xiii) 5-(2,3,4,6-tetrahydro-3-methyl-1-(2-methylpropyl)-6-(1-naphthalenylmethyl)-2,4dioxo-1H-pyrrolo[3,4-d]pyrimidin-5-yl)pent-3-enoic acid;

(xiv) 5-(5-hydroxypent-1-ynyl)-3-methyl-1-(2-methylpropyl)-6-(1-naphthalenylmethyl)-1H-pyrrolo[3,4-d]pyrimidine-2,4(3H,6H)-dione;

(xv) 5-(5-hydroxypentyl)-3-methyl-1-(2-methylpropyl)-6-(1-naphthalenylmethyl)-1H-pyrrolo[3,4-d]pyrimidine-2,4(3H,6H)-dione;

(xvi) 5-(4-hydroxybut-1-ynyl)-3-methyl-1-(2-methylpropyl)-6-(1-naphthalenylmethyl)-1H-pyrrolo[3,4-d]pyrimidine-2,4(3H,6H)-dione;

(xvii) 5-(4-hydroxybutyl)-3-methyl-1-(2-methylpropyl)-6-(1-naphthalenylmethyl)-1H-pyrrolo[3,4-d]pyrimidine-2,4(3H,6H)-dione;

(xviii) 5-(2,3,4,6-tetrahydro-3-methyl-1-(2-methylpropyl)-6-(1-naphthalenylmethyl)-2,4dioxo-1H-pyrrolo[3,4-d]pyrimidin-5-yl)pentanoic acid;

(xix) 4-[(2,3,4,6-tetrahydro-3-methyl-1-(2-methylpropyl)-6-(1-naphthalenylmethyl)-2,4dioxo-1H-pyrrolo[3,4-d]pyrimidin-5-yl)thio]butanenitrile;

(xx) 5-[(3-{1H-tetrazol-5-yl}propyl)thio]-3-methyl-1-(2-methylpropyl)-6-(1-naphthalenylmethyl)-1H-pyrrolo[3,4-d]pyrimidine-2,4(3H,6H)-dione;

(xxi) 3-methyl-1-(2-methylpropyl)-6-(1-naphthalenylmethyl)-5-[(2-pyridinyl)thio]-1H-pyrrolo[3,4-d]pyrimidine-2,4(3H,6H)-dione;

(xxii) 3-methyl-1-(2-methylpropyl)-6-(1-naphthalenylmethyl)-5[(2-pyridinyl)sulphinyl]-1H-pyrrolo[3,4-d]pyrimidine-2,4(3H,6H)-dione;

(xxiii) 3-methyl-1-(2-methylpropyl)-6-(1-naphthalenylmethyl)-5[(4-pyridinyl)thio]-1H-pyrrolo[3,4-d]pyrimidine-2,4(3H,6H)-dione;

(xxiv) 5-[(3-methoxyphenyl]thio)-3-methyl-1-(2-methylpropyl)-6-(1-naphthalenylmethyl)-1H-pyrrolo[3,4-d]pyrimidine-2,4(3H,6H)-dione;

(xxv) 5-[(3-hydroxyphenyl]thio)-3-methyl-1-(2-methylpropyl)-6-(1-naphthalenylmethyl)-1H-pyrrolo[3,4-d]pyrimidine-2,4(3H,6H)-dione;

(xxvi) 5-[(4-methoxyphenyl]thio)-3-methyl-1-(2-methylpropyl)-6-(1-naphthalenylmethyl)-1H-pyrrolo[3,4-d]pyrimidine-2,4(3H,6H)-dione;

(xxvii) 5-[(4-hydroxyphenyl]thio)-3-methyl-1-(2-methylpropyl)-6-(1-naphthalenylmethyl)-1H-pyrrolo[3,4-d]pyrimidine-2,4(3H,6H)-dione;

(xxviii) 5-[(2-methoxyphenyl]thio)-3-methyl-1-(2-methylpropyl)-6-(1-naphthalenylmethyl)-1H-pyrrolo[3,4-d]pyrimidine-2,4(3H,6H)-dione; and (xxix) 5-[(2-hydroxyphenyl]thio)-3-methyl-1-(2-methylpropyl)-6-(1-naphthalenylmethyl)-1H-pyrrolo[3,4-d]pyrimidine-2,4(3H,6H)-dione.

According to the invention there is also provided a process for the preparation of a compound of formula I which comprises:

(a) when X represents $S(O)_n$ and n is 1 or 2, oxidising a compound of general formula

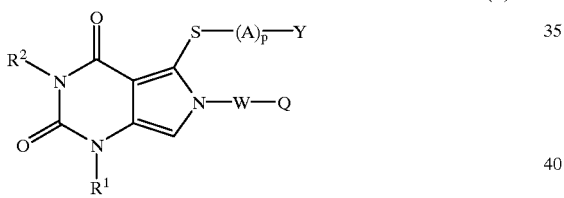

(II)

wherein $R^1$, $R^2$, A, p, Y, W and Q are as hereinbefore defined including the provisos, in the presence of an appropriate quantity of a suitable oxidising agent (e.g. 3-chloroperoxybenzoic acid or potassium peroxymonosulphate, commercially sold under the trade mark "OXONE") and an appropriate organic solvent (e.g. dichloromethane) under conditions which are well known to those skilled in the art;

(b) when Y represents $OR^{11}$ and $R^{11}$ represents $C_{1-5}$ alkyl, reacting a corresponding compound of formula (I) in which Y represents OH, with an alkyl halide of general formula

$R^{11a}Hal$ (III)

wherein $R^{11a}$ represents $C_{1-5}$ alkyl and Hal represents a halogen atom such as bromine or iodine, for example, at 25° C. in the presence of a suitable base (e.g. sodium hydride) and a suitable organic solvent (e.g. tetrahydrofuran);

(c) when Y represents $CO_2R^{12}$ and $R^{12}$ represents $C_{1-5}$ alkyl, esterifying a corresponding compound of formula (I) in which Y represents $CO_2H$ with an alcohol of general formula

$R^{12a}OH$ (IV)

wherein $R^{12a}$ represents $C_{1-5}$ alkyl, under conditions that are well known to those skilled in the art;

(d) when Y represents $CONR^{13}R^{14}$, reacting a corresponding compound of formula (I) in which Y represents $CO_2H$ with an amine of general formula

$R^{13}R^{14}NH$ (V)

wherein $R^{13}$ and $R^{14}$ are as hereinbefore defined, for example, at 25° C. in the presence of an appropriate peptide synthesis agent (e.g. diisopropylcarbodiimide and N,N-dimethyl-aminopyridine or, alternatively, ethyl chloroformate and triethylamine) and a suitable organic solvent (e.g. dichloromethane);

(e) when Y represents $CO_2H$, hydrolysing a corresponding compound of formula (I) in which Y represents $CO_2R^{12}$ and $R^{12}$ represents $C_{1-5}$ alkyl, using a suitable base (e.g. lithium or sodium hydroxide) in a suitable solvent (e.g. aqueous tetrahydrofuran) at a temperature of from 0° to 80° C.;

(f) when X represents S, A represents a $C_{1-6}$ alkylene group, Y represents $CO_2R^{12}$ and $R^{12}$ represents $C_{1-5}$ alkyl, reacting a compound of general formula

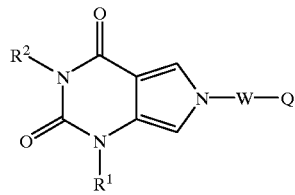

(VI)

in which $R^1$, $R^2$, W and Q are as hereinbefore defined, with a compound of general formula

$L-S-A-C(OR^{12})_3$ (VII)

wherein L is a suitable leaving group, for example para-toluenesulphinate, and A and $R^{12}$ are as hereinbefore defined, in the presence of a suitable base, for example lithium diisopropylamide, in an appropriate solvent, for example tetrahydrofuran, at from −78° C. to room temperature, followed by hydrolysis of the resulting ortho ester;

(g) when X represents S, A represents a $C_{2-6}$ alkylene group, Y represents $NR^{15}R^{16}$ and $R^{15}$ and $R^{16}$ are as hereinbefore defined, reducing a corresponding compound of formula (II) as hereinbefore defined in which A represents a $C_{1-5}$ alkylene group, Y represents $CONR^{13}R^{14}$ and $R^{13}$ and $R^{14}$ are respectively equal to $R^{15}$ and $R^{16}$, with a suitable reducing agent, for example diborane, in a suitable solvent, for example tetrahydrofuran;

(h) when X represents S, A represents a $C_{1-6}$ alkylene group, Y represents $NR^{15}R^{16}$ and $R^{15}$ and $R^{16}$ are as hereinbefore defined, reacting a corresponding compound of general formula

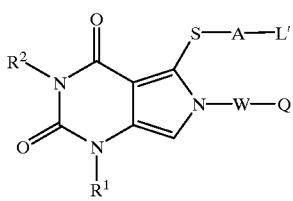

(VIII)

wherein L' represents a leaving group such as para-toluenesulphonate and $R^1$, $R^2$, A, W and Q are as hereinbefore defined, with a compound of formula (V) wherein $R^{13}$ and $R^{14}$ are respectively equal to $R^{15}$ and $R^{16}$, typically in a suitable solvent, such as dimethylformamide, in the presence of a suitable base, such as triethylamine;

(j) when X represents C≡C, CH=CH or $CH_2CH$=CH, reacting a compound of general formula

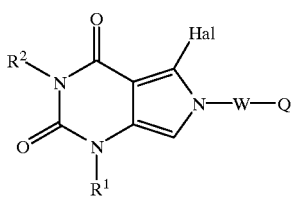

(IX)

in which Hal represents a halogen atom, e.g. bromine or iodine, and $R^1$, $R^2$, W and Q are as hereinbefore defined, with a compound of general formula (X), H—X'—(A)$_p$—Y, in which X' represents C≡C, CH=CH or CH=$CHCH_2$ and A, p and Y are as hereinbefore defined in the presence of a palladium catalyst (e.g. bis-triphenylphosphinepalladium (II) chloride), and optionally hydrogenating the compound of formula (I) obtained wherein X represents C≡C or CH=CH in the presence of a palladium on carbon catalyst to produce a further compound of formula (I) wherein X represents $(CH_2)_2$;

(k) when X represents S, A represents a $C_{1-6}$ alkylene group and Y represents CN, reacting a compound of formula (VIII) as hereinbefore defined with sodium cyanide (NaCN);

(l) when X represents S, A represents a $C_{1-6}$ alkylene group and Y represents $NHSO_2R^{17}$, reacting a corresponding compound of formula (I) in which Y represents $NH_2$ with a compound of general formula (XI), $R^{17}SO_2Cl$, wherein $R^{17}$ is as hereinbefore defined;

(m) when X represents S, A represents a $C_{1-6}$ alkylene group and Y represents $NHCOR^{18}$, reacting a corresponding compound of formula (I) in which Y represents $NH_2$ with a compound of general formula (XII), $R^{18}COCl$, wherein $R^{18}$ is as hereinbefore defined;

(n) when X represents S and Y represents an optionally substituted aryl or heteroaryl group, reacting a compound of formula (VI) as hereinbefore defined with a compound of general formula Y'—(A)$_p$—S—S—(A)$_p$—Y' (XIII)

wherein Y' represents an optionally substituted aryl or heteroaryl group and p and A are as hereinbefore defined; or (p) when X represents S, A represents a $C_{1-6}$ alkylene group and Y represents a tetrazolyl group, reacting a compound of formula (I) in which X represents S, A represents a $C_{1-6}$ alkylene group and y represents CN, with trialkyltin azide (e.g. trimethyltin axide), typically in a solvent such as toluene under reflux conditions; and optionally forming a pharmaceutically acceptable derivative thereof.

Compounds of formula (II) wherein Y represents OH may be prepared by reaction of a compound of formula (VI) as hereinbefore defined with a compound of general formula

L"—S—A—$OR^{22}$ (XIV)

wherein L" is a suitable leaving group, for example para-toluenesulphinate, A is as hereinbefore defined, and $R^{22}$ is H or a suitable protecting group such as tert-butyldimethylsilyl, in the presence of a suitable base, for example lithium diisopropylamide, in a suitable solvent, for example tetrahydrofuran at around −70° C.

Compounds of formula (II), wherein Y represents $OR^{11}$, $CO_2R^{12}$, $CONR^{13}R^{14}$, $NHSO_2R^{17}$ or $NHCOR^{18}$ and wherein $R^{11}$ or $R^{12}$ as appropriate represent $C_{1-5}$ alkyl and $R^{13}$ and $R^{14}$ or $R^{17}$ or $R^{18}$ as appropriate are as hereinbefore defined, may be prepared from corresponding compounds of formula (II) wherein Y represent OH, $CO_2H$ or $NH_2$ as appropriate in accordance with the methods described in steps (b) to (d), (l) and (m) hereinbefore.

Compounds of formula (VI) are known from *J. Med. Chem.* (1995) 38, 2557, or may be prepared analogously by methods described therein.

Compounds of formula (VIII) may be prepared from compounds of formula (II) where Y represents OH by techniques known to those skilled in the art.

Compounds of formula (IX) may be prepared by reacting a compound of formula (VI) with lithium diisopropylamide at −78° C., followed by the addition of a halogen.

Other compounds of formula (II), (III), (IV), (V), (VII), (X), (XI), (XII), (XIII) and (XIV) are either commercially available, are well known in the literature or may be prepared easily using known techniques.

It will be appreciated by those skilled in the art that in the processes described above the functional groups (e.g. hydroxy or amino groups) of intermediate compounds may need to be protected by protecting groups. The final stage in the preparation of the compounds of formula (I) may involve the removal of one or more protecting groups.

The protection and deprotection of functional groups is fully described in 'Protective Groups in Organic Chemistry', edited by J. W. F. McOmie, Plenum Press (1973), and 'Protective Groups in Organic Synthesis', 2nd edition. T. W. Greene & P. G. M. Wuts, Wiley-Interscience (1991).

Pharmaceutically acceptable derivatives of the compounds of formula (I) include solvates and salts.

Salts of the compounds of formula (I) may be formed by reacting the free acid, or a salt thereof, or the free base, or a salt or derivative thereof, with one or more equivalents of the appropriate base or acid. The reaction may be carried out in a solvent or medium in which the salt is insoluble or in a solvent in which the salt is soluble, e.g. ethanol, tetrahydrofuran or diethyl ether, which may be removed in vacuo, or by freeze drying. The reaction may also be a metathetical process or it may be carried out on an ion exchange resin. The non-toxic physiologically acceptable salts are preferred, although other salts may be useful, e.g. in isolating or purifying the product.

Particular salts which may be mentioned include sodium, potassium, hydrochloride, hydrobromide, sulphonate, tosylate and methanesulphonate.

The compounds of formula (I) may exhibit tautomerism. All tautomeric forms and mixtures thereof are included within the scope of the invention.

The compounds of formula (I) have a number of chiral centres and may exist in a variety of stereoisomers. The invention provides all optical and stereoisomers, as well as racemic mixtures. The isomers may be resolved or separated by conventional techniques, e.g. chromatography or fractional crystallisation. Enantiomers may be isolated by separation of a racemic or other mixture of the compounds using conventional, e.g. chiral HPLC, techniques. Alternatively the desired optical isomers may be made by reaction of the appropriate optically active starting materials under conditions which will not cause racemisation, or by derivatisation, for example with a homochiral acid followed by separation of the diastereomeric derivatives by conventional means (e.g. HPLC, chromatography over silica) or may be made with achiral starting materials and chiral reagents. All stereoisomers are included within the scope of the invention.

The compounds of formula (I) may be isolated from their reaction mixtures using conventional techniques.

The compounds of formula (I) are useful because they possess pharmacological activity in human and non-human animals. They are therefore indicated as pharmaceuticals. In particular they are useful because they possess immunosuppressive activity, for example as demonstrated in the test described below.

The compounds are thus indicated for use in the treatment or prevention of resistance to transplanted organs or tissues, such as kidney, heart, lung, bone marrow, skin and cornea; and of autoimmune, inflammatory, proliferative and hyperproliferative diseases including cancer, and of cutaneous manifestations of immunologically-mediated diseases: for example rheumatoid arthritis, lupus erythematosus, systemic lupus erythematosus, Hashimoto's thyroiditis, multiple sclerosis, myasthenia gravis, type 1 diabetes, uveitis, nephrotic syndrome, psoriasis, atopical dermatitis, contact dermatitis and further eczematous dermatitides, seborrhoeic dermatitis, Lichen planus, Pemphigus, bullous Pemphigoid, Epidermolysis bullosa, urticaria, angioedemas, vasculitides, erythemas, cutaneous eosinophilias, Alopecia areata, eosinophilic fasciitis and atherosclerosis.

The compounds of formula (I) are also indicated in the treatment of respiratory diseases, for example sarcoidosis, farmer's lung and related diseases, fibroid lung, idiopathic interstitial pneumonia and reversible obstructive airways diseases which latter includes conditions such as asthma (e.g. bronchial asthma, allergic asthma, intrinsic asthma, extrinsic asthma and dust asthma), particularly chronic or inveterate asthma (e.g. late asthma and airway hyperresponsiveness) and bronchitis.

Further, the compounds of formula (I) are indicated in the treatment of a disease selected from intestinal inflammations/allergies such as Coeliac disease, proctitis, eosinophilic gastro-enteritis, mastocytosis, Crohn's disease and ulcerative colitis; and food related allergic diseases which have symptomatic manifestation remote from the gastrointestinal tract, for example, migraine, rhinitis and eczema.

For the above-mentioned therapeutic uses the dosage administered will, of course, vary with the compound employed, the mode of administration, the treatment desired and the disease indicated.

The compounds of formula (I) and pharmaceutically acceptable derivatives thereof, may be used on their own but will generally be administered in the form of a pharmaceutical composition in which the compound or derivative (active ingredient) is in admixture with a pharmaceutically acceptable adjuvant, diluent or carrier. The pharmaceutical composition will preferably comprise from 0.05 to 80% w (percent by weight), more preferably from 0.10 to 50% w, of active ingredient, and, from 20 to 99.95% w, more preferably from 50 to 99.90% w, of a pharmaceutically acceptable adjuvant, diluent or carrier.

Thus, the present invention also provides a pharmaceutical composition comprising a compound of formula (I), or a pharmaceutically acceptable derivative thereof, in admixture with a pharmaceutically acceptable adjuvant, diluent or carrier.

The invention further provides a process for the preparation of a pharmaceutical composition according to the invention which comprises admixing a compound of formula (I), or a pharmaceutically acceptable derivative thereof, with a pharmaceutically acceptable adjuvant, diluent or carrier.

According to a further aspect of the invention, there is provided a method of effecting immunosuppression which comprises administering a therapeutically effective amount of a compound of formula (I), or a pharmaceutically acceptable derivative thereof, to a patient.

The invention also provides a method of treating, or reducing the risk of, a reversible obstructive airways disease in a patient suffering from, or at risk of, said disease, which comprises administering to the patient a therapeutically effective amount of a compound of formula (I), or a pharmaceutically acceptable derivative thereof.

The invention will be further illustrated by reference to the following examples in which MS and NMR are the abbreviations for Mass Spectrometry and Nuclear Magnetic Resonance respectively.

EXAMPLE 1

5-[(3-Hydroxypropyl)sulphinyl]-3-methyl-1-(2-methylpropyl)-6-(1-naphthalenylmethyl)-1H-pyrrolo[3,4-d]pyrimidine-2,4(3H,6H)-dione (1) and 5-[(3-hydroxypropyl)sulphonyl]-3-methyl-1-(2-methylpropyl)-6-(1-naphthalenylmethyl)-1H-pyrrolo[3,4-d]pyrimidine-2,4(3H,6H)-dione (2)

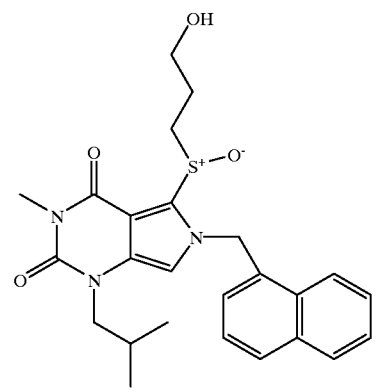

-continued (2)

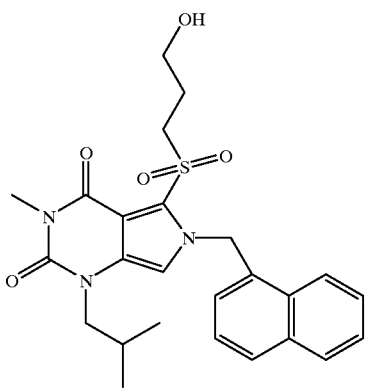

To a stirred solution of 5-[(3-hydroxypropyl)thio]-3-methyl-1-(2-methylpropyl)-6-(1-naphthalenylmethyl)-pyrrolo-[3,4-d]-pyrimidine-2,4-dione (0.39 g; 0.864 mmol; *J. Med. Chem.* (1995) 38, 2557) in dichloromethane (20 ml) was added 3-chloro-peroxybenzoic acid (55–60%; 0.526 g). After 30 minutes the reaction was diluted with dichloromethane (80 ml) and washed with sodium bicarbonate solution (50 ml) containing sodium metabisulphite (1 g). The organic layer was dried over magnesium sulphate (MgSO$_4$), concentrated in vacuo and chromatographed on silica eluting with hexane:acetone (3:2) to give separately the two title compounds which were each subsequently recrystallised with hexane:ethyl acetate [1:2].

Title Compound 1
  Melting point: 204–206° C.
  Elemental Analysis (in %):
  Theory: C 64.22, H 6.25, N 8.99, S 6.86
  Found: C 64.10, H 6.51, N 9.22, S 6.53
  MS(FAB) 468 (M+H)$^+$
Title Compound 2
  Melting point: 201–202° C.
  Elemental Analysis (in %):
  Theory: C 62.09, H 6.04, N 8.69, S 6.63
  Found: C 61.84, H 6.21, N 8.62, S 6.22
  MS(FAB) 484 (M+H)$^+$

EXAMPLE 2

Methyl 4-[(2,3,4,6-tetrahydro-3-methyl-1-(2-methylpropyl)-6-(1-naphthalenylmethyl)-2,4-dioxo-1H-pyrrolo[3,4-d]pyrimidin-5-yl)thio]butanoate

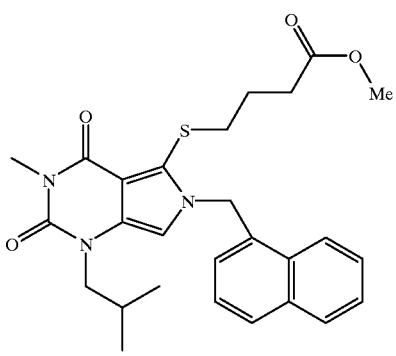

a) 4,4,4-Trimethoxybutyl para-toluenethiosulphonate

A mixture of para-toluenethiosulphonic acid potassium salt (24 mmol), trimethyl 4-bromoorthobutyrate (22 mmol) and hexamethylphosphoramide (30 ml) was stirred at room temperature for 48 h before being poured into 10:1 hexane/diethyl ether (500 ml) and shaken vigorously. The mixture was washed with water (2×200 ml) and then brine. The organic phase was collected and dried over magnesium sulphate (MgSO$_4$) and evaporated to dryness in vacuo to yield the sub-title ester as an oil (5.3 g) containing ca 7% 4,4,4-trimethoxybutylparatoluene(dithioperoxy)sulphonate.

$^1$H NMR (CDCl$_3$) δ 1.95 (2H, m), 2.37 (2H, t), 2.44 (3H, s), 3.02 (2H, t), 3.16 (9H, s), 7.33 (2H, d), 7.80 (2H, d)

b) Methyl 4-[(2,3,4,6-tetrahydro-3-methyl-1-(2-methylpropyl)-6-(1-naphthalenylmethyl)-2,4-dioxo-1H-pyrrolo[3,4-d]pyrimidin-5-yl)thio]butanoate To a solution of 3-methyl-1-(2-methylpropyl)-6-(1-naphthalenylmethyl)-1H-pyrrolo[3,4-d]pyrimidine-2,4(3H,6H)-dione (1.4 mmol) in tetrahydrofuran (4 ml) at −78° C. under nitrogen was added a freshly prepared 1M solution of lithium diisopropylamide (8.5 mmol) in tetrahydrofuran followed by 4,4,4-trimethoxybutyl para-toluenethiosulphonate (2.3 mmol). The reaction was allowed to warm to room temperature and then quenched via addition of saturated aqueous NH$_4$Cl and then brine. The mixture was extracted into diethyl ether which was collected, dried over magnesium sulphate (MgSO$_4$) and evaporated to dryness in vacuo. The residual oil was redissolved in methanol/water and treated with glacial acetic acid for 0.5 h. The reaction was then basified via addition of solid sodium hydrogencarbonate. The mixture was extracted into diethyl ether, washed with brine, dried over magnesium sulphate (MgSO$_4$) and evaporated to dryness in vacuo. The resultant oil was chromatographed twice (silica) eluting with 1:3 hexanes/diethyl ether to yield the title compound as an oil (133 mg).

MS (APCI+ve) 464 (M+H)$^+$ $^1$H NMR (CDCl$_3$) δ 0.88 (6H, d), 1.85 (2H, m), 2.12 (1H, m), 2.40 (2H, m), 3.04 (2H, m), 3.42 (3H, s), 3.55 (2H, d), 3.62 (3H, s), 5.84 (2H, s), 6.35 (1H, s), 6.80 (1H, d), 7.39 (1H, t), 7.57 (2H, m), 7.82 (1H, d), 7.91 (2H, m)

EXAMPLE 3

5-[(3-Methoxypropyl)thio]-3-methyl-1-(2-methylpropyl)-6-(1-naphthalenylmethyl)-1H-pyrrolo[3,4-d]pyrimidine-2,4(3H,6H)-dione

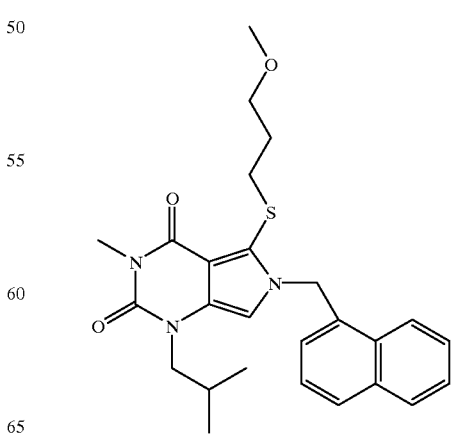

To a 60% dispersion of sodium hydride in mineral oil (0.035 g, 0.886 mmol) under nitrogen, was added a solution of 5-[3-hydroxypropyl)thio]-3-methyl-1-(2-methylpropyl)-6-(1-naphthalenylmethyl)-1H-pyrrolo[3,4-d]pyrimidine-2,4 (3H,6H)-dione (0.20 g) in anhydrous tetrahydrofuran (10 ml). The mixture was stirred at room temperature for 30 minutes, iodomethane (0.055 ml) was added, and stirring was continued for 18 hours. The mixture was added to saturated sodium bicarbonate solution (20 ml) and extracted with ethyl acetate (20 ml). The organic extracts were dried over anhydrous magnesium sulphate, filtered and evaporated under reduced pressure. The residue was purified by column chromatography over silica eluting with hexane:acetone (4:1), and then by column chromatography over silica, eluting with hexane:ethyl acetate (2:1). The resulting oil was crystallised from an ethyl acetate/hexane mixture to give the title compound (95 mg).

Melting point: 92–94° C.

MS (FAB) 466 (M+H)$^+$ $^1$H NMR (CDCl$_3$) δ 0.87 (6H, d), 1.81 (2H, quin), 2.12 (1H, m), 3.07 (2H, t), 3.25 (3H, s), 3.38 (2H, t), 3.43 (3H, s), 3.54 (2H, d), 5.84 (2H, s), 6.34 (1H, s), 6.82 (1H, d), 7.39 (1H, t), 7.53–7.59 (2H, m), 7.83 (1H, d), 7.91–7.93 (2H, m)

EXAMPLE 4

5-[(2-Hydroxyethyl)sulphinyl]-3-methyl-1-(2-methylpropyl)-6-(1-naphthalenylmethyl)-1H-pyrrolo[3,4-d]pyrimidine-2,4(3H,6H)-dione

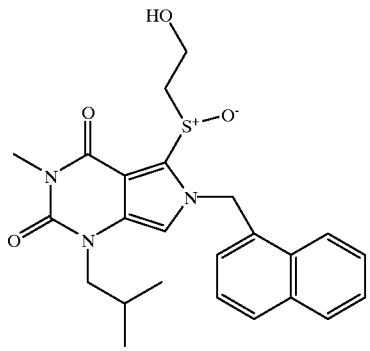

a) Bis-[dimethyl(1,1-dimethyl)silyloxyethyl] Disulphide

To a stirred solution of 2-hydroxyethyl disulphide (2 g) and imidazole (5.3 g) in dichloromethane (100 ml) was added dimethyl(1,1-dimethylethyl)silyl chloride. The solution was stirred overnight and then diluted with diethyl ether. The mixture was washed with dilute hydrochloric acid, then with sodium bicarbonate solution and then dried over magnesium sulphate. Concentration in vacuo followed by chromatography on silica gel (hexane:diethyl ether/20:1) gave the subtitle compound as a clear oil (3.75 g).

MS (EI) 382 ((M–CH$_3$)$^+$).

b) 5-(2-Hydroxyethyl)thio-3-methyl-1-(2-methylpropyl)-6-(1-naphthalenylmethyl-1H-pyrrolo[3,4-d]pyrimidine-2,4(3H,6H)-dione To a stirred solution of 3-methyl-1-(2-methylpropyl)-6-(1-naphthalenylmethyl)-pyrrolo[3,4-d]pyrimidine-4,6-dione ((J. Med. Chem., 1995, 38, 2557; 0.50 g) and bis-[dimethyl(1,1-dimethylethyl)silyloxyethyl]disulphide (1.06 g) in anhydrous tetrahydrofuran (15 ml) at –78° C. was added dropwise a solution of lithium diisopropylamide (2.78 mmol) in tetrahydrofuran (5 ml). The solution was stirred for a further 0.5 h at –78° C. and then allowed to warm to ambient temperature. Saturated aqueous sodium bicarbonate solution (10 ml) was added and the solution was extracted with ethyl acetate. The organic extracts were dried over magnesium sulphate and concentrated in vacuo. The residue was redissolved in acetonitrile (10 ml) and treated with 40% aqueous hydrofluoric acid at ambient temperature. The solution was stirred for 1 hour, then neutralised with aqueous sodium bicarbonate solution and extracted with ethyl acetate. The organic extracts were dried over magnesium sulphate and concentrated in vacuo. Chromatography on silica gel (diethyl ether) gave the subtitle compound (0.47 g) as a white solid.

Melting point: 138–141° C.

MS (FAB) 353 ((M+H)$^+$).

c) 5-[(2-Hydroxyethyl)sulphinyl]-3-methyl-1-(2-methylpropyl)-6-(1-naphthalenylmethyl-1H-pyrrolo[3,4-d]pyrimidine-2,4(3H,6H)-dione To a stirred solution of 5-(2-hydroxyethyl)thio-3-methyl-1-(2-methylpropyl)-6-(1-naphthalenylmethyl-1H-pyrrolo[3,4-d]pyrimidine-2,4(3H,6H)-dione (100 mg) in methanol (20 ml) was added potassium peroxymonosulphate (commercially sold under the trade mark "OXONE") (300 mg) in water (10 ml). After stirring for 10 minutes the reaction mixture was diluted with water and extracted with ethyl acetate. The organic extracts were dried over magnesium sulphate and concentrated in vacuo. Chromatography on silica gel (ethyl acetate) gave the title compound (70 mg) as a white foam.

MS (FAB) 454 ((M+H)$^+$).

$^1$H NMR (CDCl$_3$) δ 0.85 (3H, d), 0.87 (3H, d), 2.05–2.13 (1H, m), 3.21–3.33 (1H, m), 3.36 (3H, s), 3.49–3.61 (2H, m), 3.65–3.73 (1H, m), 3.84–4.05 (2H, m), 6.17–6.27 (2H, m), 6.42 (1H, s), 6.95 (1H, d), 7.44 (1H, t), 7.54–7.66 (2H, m) and 7.87–7.98 (3H, m).

EXAMPLE 5

4-[(2,3,4,6-Tetrahydro-3-methyl-1-(2-methylpropyl)-6-(1-naphthalenylmethyl)-2,4-dioxo-1H-pyrrolo[3,4-d]pyrimidin-5-yl)thio]butanoic Acid

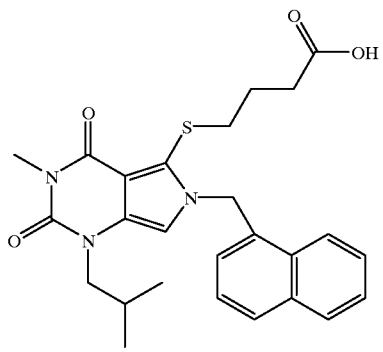

The compound of Example 2, methyl 4-[(2,3,4,6-Tetrahydro-3-methyl-1-(2-methylpropyl)-6-(1-naphthalenylmethyl)-2,4-dioxo-1H-pyrrolo[3,4-d]-pyrimidin-5-yl)thio]butanoate (400 mg), was dissolved in 3:1:1 tetrahydrofuran/methanol/1M lithium hydroxide and stirred for 1.5 h before being acidified by dropwise addition of concentrated hydrochloric acid (HCl). The mixture was then extracted with ethyl acetate. The organic phase was washed with brine, dried over magnesium sulphate (MgSO$_4$) and evaporated to dryness in vacuo. The resultant yellow oil was chromatographed (silica), eluting with 200:10:1 dichloromethane/methanol/glacial acetic acid. The resultant red oil was dissolved in toluene and then evaporated, then similarly with trichloromethane to yield a pink foam. The foam was recrystallised from ethyl acetate/hexane to yield 129 mg of the title compound.

MS (APCI+ve) (M+H)$^+$480

Elemental Analysis (in %):

Theory: C 65.11, H 6.10, N 8.76, S 6.69

Found: C 65.15, H 6.24, N 8.83, S 6.70

$^1$H NMR (CDCl$_3$) δ 0.88 (6H, d), 1.85 (2H, quin), 2.10 (1H, m), 2.47 (2H, t), 3.02 (2H, t), 3.42 (3H, s), 3.55 (2H, d), 5.84 (2H, s), 6.37 (1H, s), 6.79 (1H, d), 7.38 (1H, t), 7.56 (2H, m), 7.82 (1H, d), 7.91 (2H, m)

EXAMPLE 6

4-[(2,3,4,6-Tetrahydro-3-methyl-1-(2-methylpropyl)-6-(1-naphthalenylmethyl)-2,4-dioxo-1H-pyrrolo[3,4-d]pyrimidin-5-yl)thio]butanoic Acid, Sodium Salt

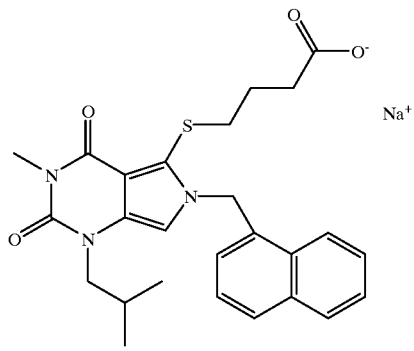

The compound of Example 5, 4-[(2,3,4,6-tetrahydro-3-methyl-1-(2-methylpropyl)-6-(1-naphthalenylmethyl)-2,4-dioxo-1H-pyrrolo[3,4-d]pyrimidin-5-yl)thio]butanoic acid (200 mg), was dissolved in dioxane (5 ml) and sodium hydroxide solution (2.5 M) (0.163 ml) was added. The solvent was removed by evaporation and freeze drying to give the title compound as a 1:1 mixture with sodium carbonate.

Elemental Analysis for C$_{27}$H$_{28}$N$_3$Na$_3$O$_7$S (in %):

Theory: C 53.37, H 4.65, N 6.92, S 5.28

Found: C 53.51, H 5.15, N 6.65, S 5.07

Melting Point: >163° C. slow melt

MS (APCI) 480 (M+H)$^+$ $^1$H NMR (DMSO) δ 0.85 (6H,d), 1.4–1.6 (2H,m), 1.80 (2H,t), 2.0–2.2 (1H,m), 2.88 (2H,t), 3.57 (2H,d), 5.89 (2H, s), 6.57 (1H,d), 7.12 (1H,s), 7.41 (1H,t), 7.5–7.7 (2H,m), 7.86 (1H,d), 7.99 (1H,d), 8.18 (1H,d)

EXAMPLE 7

5-[(2-Dimethylaminoethyl)thio]-3-methyl-1-(2-methylpropyl)-6-(1-naphthalenylmethyl)-1H-pyrrolo[3,4-d]pyrimidine-2,4(3H,6H)-dione

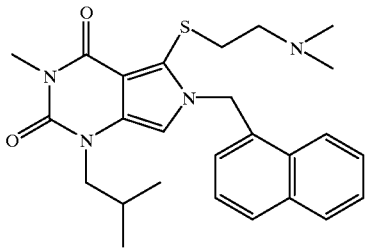

3-Methyl-1-(2-methylpropyl)-6-(1-naphthalenylmethyl)-1H-pyrrolo-[3,4-d]pyrimidine-2,4(3H,6H)-dione (J. Med. Chem., 1995, 38 2557) (473 mg) and bis(2-dimethylaminoethyl)disulphide (0.6 ml) were dissolved in tetrahydrofuran (10 ml) and cooled to −78° C. Lithium diisopropylamide in tetrahydrofuran (2.5 eq) was added dropwise and the resultant deep red solution was stirred for 75 minutes at −78° C. The cooling bath was removed and the solution allowed to stir for a further 60 minutes. Sodium bicarbonate (aqueous) was added followed by ether and the phases were separated. The aqueous phase was extracted twice with ether. The organic phases were combined and washed twice with brine before being dried, filtered and concentrated. The resultant oil was purified by column chromatography (eluant, dichloromethane:methanol:triethylamine 450:50:0.2) and then recrystallised from ether-isohexane to give the title compound (230 mg).

Melting point: 140–144° C.

MS (APCI+ve) 465 (M+H)$^+$ $^1$H NMR (DMSO d6) δ 0.87 (6H, d), 2.01 (6H, s), 2.10–2.16 (1H, m), 2.25 (1H, t), 2.99 (2H, t), 3.25 (3H, s), 3.59 (2H, d), 5.92 (2H, s), 6.54 (1H, d), 7.18 (1H, s), 7.41 (1H, t), 7.58–7.67 (2H, m), 7.86 (1H, d), 7.99 (1H, d), 8.17 (1H, d)

EXAMPLE 8

6-(2,3-Dihydro-1H-inden-2-yl)-5-[(3-hydroxypropyl)sulphinyl]-3-methyl-1-(1-methylethyl)-1H-pyrrolo[3,4-d]pyrimidine-2,4(3H,6H)-dione

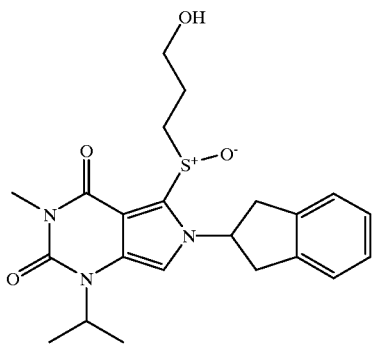

a) 6-(2,3-Dihydro-1H-inden-2-yl)-3-methyl-1-(1-methylethyl)-1H-pyrrolo-[3,4-d]pyrimidine-2,4(3H,6H)-dione 3,6-Dimethyl-5-formyl-1-(1-methylethyl)pyrimidine-2,4-dione (J. Med. Chem., 1995, 38, 2557; 1.70 g) was dissolved in chloroform (25 ml) and the solution was heated to 50° C. A solution of bromine (0.413 ml) in chloroform (20 ml) was added dropwise to the aldehyde solution over 24 minutes. The reaction was maintained at 50° C. for a further 15 minutes, then allowed to cool to ambient temperature. The reaction mixture was diluted with dichloromethane and was washed successively with water, dilute sodium thiosulphate solution (twice) and brine. The resultant solution was dried, filtered and evaporated to a crude oil which was dissolved in ethanol (50 ml). Triethylamine (3.38 ml) was added to the solution followed by 2-aminoindane (1.49 g) and the mixture was stirred under nitrogen overnight. The reaction mixture was filtered, the white solid collected was washed with a little ethanol and the filtrate was evaporated to give a brown oil. Ethyl acetate was added to the oil and the resultant precipitate was collected by filtration and was washed with a little ethyl acetate. The filtrate was washed with hydrochloric acid (HCl) (2.5 M) and then brine. The resultant ethyl acetate phase was dried, filtered and evaporated to an oil. The oil was purified by chromatography, eluting with isohexane:acetone (4:1) to give a solid which was triturated with hot ethyl acetate:isohexane (3:1) to give the subtitle compound (0.50 g).

Melting point: 158–160° C.

MS (APCI+ve) 3.24 (M+H)$^+$ b) 6-(2,3-Dihydro-1H-inden-2-yl)-5-[(3-hydroxypropyl)thio]-3-methyl-1-(1-methylethyl)-1H-pyrrolo[3,4-d]pyrimidine-2,4(3H,6H)-dione 6(2,3-Dihydro-1H-inden-2-yl)-3-methyl-1-(1-methylethyl)-1H-pyrrolo-[3,4-d]pyrimidine-2,4(3H,6H)-dione (165 mg) and S-{3-[1,1-dimethylethyl)-dimethylsilyl]oxypropyl} toluenethiosulphonate (J. Med. Chem., 1995, 38, 2557) (362 mg) were dissolved in tetrahydrofuran (6 ml) and the resulting solution was cooled to –78° C. Lithium diisopropylamide in tetrahydrofuran (3 eq) was added dropwise to the cold solution and the resulting solution was stirred for 75 minutes at –78° C. and then the cooling bath was removed. The solution was stirred for a further 75 minutes and then sodium bicarbonate (aqueous) was added. The reaction mixture was extracted thrice with ether. The organic phases were combined and washed twice with brine before being dried, filtered and evaporated. The resultant oil was purified by column chromatography (eluant, isohexane-:ethyl acetate 7:2).

The product was dissolved in acetonitrile (10 ml) and hydrofluoric acid (40%, 6 drops) was added. The solution was stirred at ambient temperature for 30 minutes then sodium bicarbonate (aqueous) was added. Ether-ethyl acetate mixture (ca 1:1) was added to the reaction mixture and the phases were separated. The aqueous phase was extracted twice with ether-ethyl acetate mixtures. The organic phases were combined and washed twice with brine before being dried, filtered and concentrated. Crystallisation from ether-cyclohexane gave the subtitle compound (141 mg).

Melting point: 123–125° C.

MS (APCI+ve) 414 (M+H)$^+$ c) 6-(2,3-Dihydro-1H-inden-2-yl)-5-[(3-hydroxypropyl)sulphinyl]-3-methyl-1-(1-methylethyl)-1H-pyrrolo[3,4-d]pyrimidine-2,4(3H,6H)-dione 6-(2,3-Dihydro-1H-inden-2-yl)-5-[(3-hydroxypropyl)thio]-3-methyl-1-(1-methylethyl)-1H-pyrrolo[3,4-d]pyrimidine-2,4(3H,6H)-dione (100 mg) was dissolved in methanol (40 ml). Water (10 ml) and potassium peroxymonosulphate (commercially sold under the trade mark "OXONE") (185 mg) were added and the solution was stirred for 15 minutes. The reaction mixture was diluted with water and then extracted with ethyl acetate thrice. The extracts were combined, washed with brine, then dried, filtered and the solvent was evaporated. The resultant oil was triturated with isohexane, then recrystallised from ethyl acetate-isohexane mixtures to give the title compound (15 mg).

Melting point: 164–165° C.

MS (APCI+ve) 430 (M+H)$^+$ $^1$H (DMSO d6) δ 1.35 (6H, d), 1.73 (2H, quin), 3.19 (3H, s), 3.26–3.56 (8H, m), 4.65 (1H, t), 4.71 (1H, sept), 6.08–6.12 (1H, m), 7.22–7.32 (4H, m), 7.50 (1H, s)

EXAMPLE 9

6-(2,3-Dihydro-1H-inden-2yl)-5-[(3-hydroxypropyl)sulphonyl]-3-methyl-1-(1-methylethyl)-1H-pyrrolo[3,4-d]pyrimidine-2,4(3H,6H)-dione

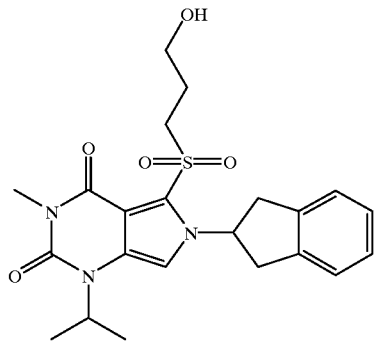

The compound of Example 8, 6-(2,3-Dihydro-1H-inden-2-yl)-5-[(3-hydroxypropyl)sulphinyl]-3-methyl-1-(1-methylethyl)-1H-pyrrolo[3,4-d]pyrimidine-2,4(3H,6H)-dione (80 mg), was dissolved in dichloromethane (5 ml) and 3-chloroperoxybenzoic acid (57–85%) (50 mg) was added. The reaction mixture was stirred for 75 minutes then water and sodium metabisulphite (45 mg) were added and the mixture was stirred for 5 minutes. The phases were separated and the organic phase was washed with sodium bicarbonate (aqueous), then dried, filtered and evaporated. The resultant foam was recrystallised from isohexane-ethyl acetate-ether to give the title compound (15 mg).

Melting point: 171–172° C.

MS (APCI+ve) 446 (M+H)$^+$ $^1$H NMR (DMSO d6) δ 1.34 (6H, d), 1.73–1.83 (2H, m), 3.22 (3H, s), 3.39–3.50 (6H, m), 3.77–3.83 (2H, m), 4.66 (1H, t), 4.64–4.72 (1H, m), 6.24 (1H, quin), 7.22–7.32 (4H, m), 7.54 (1H, s)

EXAMPLE 10

5-[(3-Hydroxypropyl)sulphinyl]-3-methyl-1-(1-methylethyl)-6-(1-naphthalenylmethyl)-1H-pyrrolo[3,4-d]pyrimidine-2,4(3H,6H)-dione

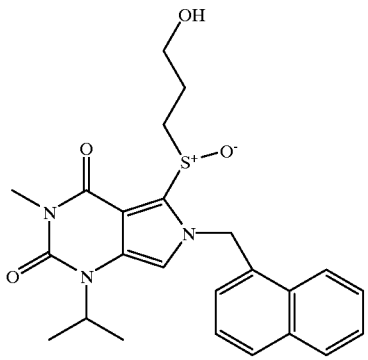

The title compound was prepared from 5-[(3-Hydroxypropyl)thio]-3-methyl-1-(1-methylethyl)-6-(1-naphthalenylmethyl)-1H-pyrrolo[3,4-d]pyrimidine-2,4(3H,6H)-dione (J. Med. Chem., 1995, 38, 2557) in a manner analogous to the method of Example 8 (c) above.

Melting point: 184–185° C.

MS (APCI+ve) (M+H)⁺

$^1$H NMR (CDCl$_3$) δ 1.35 (3H, d), 1.37 (3H, d), 1.97–2.07 (2H, m), 2.60 (1H, t), 3.24–3.51 (2H, m), 3.72–3.86 (2H, m), 4.68–4.70 (1H, m), 6.23 (2H, s), 6.48 (1H, s), 7.00 (1H, d), 7.44 (1H, t), 7.53–7.62 (2H, m), 7.86–7.94 (2H, m), 7.99–8.02 (1H, m)

EXAMPLE 11

4-[(2,3,4,6-Tetrahydro-3-methyl-1-(2-methylpropyl)-6-(1-naphthalenylmethyl)-2,4-dioxo-1H-pyrrolo[3,4-d]pyrimidin-5-yl)thio]butanamide

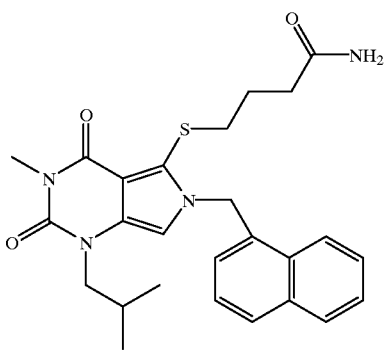

The compound of Example 5, 4-[(2,3,4,6-tetrahydro-3-methyl-1-(2-methylpropyl)-6-(1-naphthalenylmethyl)-2,4-dioxo-1H-pyrrolo[3,4-d]pyrimidin-5-yl)thio]butanoic acid (100 mg), was dissolved in tetrahydrofuran (3 ml) and the solution was cooled in ice. Triethylamine (30 μl) was added followed by ethyl chloroformate (21 μl); the ice bath was removed and the solution was allowed to stir for 15 minutes and was then cooled in ice again. Aqueous ammonia (0.88 specific gravity, 1 ml) was added and the mixture was stirred for 3 days. The mixture was poured onto water and extracted thrice with dichloromethane. The organic extracts were combined, washed with brine, dried, filtered and evaporated to give an oil which was purified by chromatography, eluting first with ethyl acetate:isohexane:acetic acid (75:25:1) and then with ethyl acetate:acetic acid (199:1) to give the title compound (70 mg).

Melting point: 162–165° C.

MS (APCI+ve) 479 (M+H)⁺

$^1$H NMR (CDCl3) δ 0.94 (6H, d), 1.86 (2H, quin), 2.12–2.16 (1H, m), 2.45 (2H, t), 2.90 (2H, t), 3.41 (3H, t), 3.56 (2H, d), 5.30 (1H, br), 5.86 (2H, s), 6.08 (1H, br), 6.39 (1H, s), 6.81 (1H, d), 7.40 (1H, dd), 7.58 (2H, m), 7.84 (1H, d), 7.91 (2H, m)

EXAMPLE 12

5-(2,3,4,6-Tetrahydro-3-methyl-1-(2-methylpropyl)-6-(1-naphthalenylmethyl)-2,4-dioxo-1H-pyrrolo[3,4-d]pyrimidin-5-yl)pent-3-enoic Acid

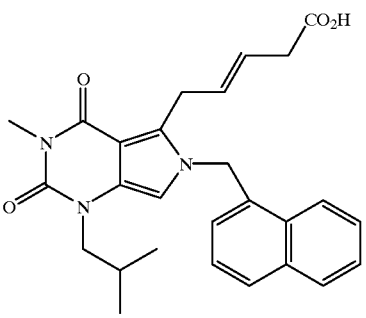

a) 5-Iodo-3-methyl-1-(2-methylpropyl)-6-(1-naphthalenylmethyl)-1H-pyrrolo-[3,4-d]pyrimidine-2,4(3H,6H)-dione 3-Methyl-1-(2-methylpropyl)-6-(1-naphthalenylmethyl)-1H-pyrrolo-[3,4-d]pyrimidine-2,4(3H,6H)-dione ((J. Med. Chem., 1995, 38, 2557; 500 mg) was dissolved in tetrahydrofuran (15 ml) and cooled to −78° C. A solution of lithium diisopropylamide (2 eq) in tetrahydrofuran (5 ml) was added dropwise with stirring at −78° C. Iodine (350 mg) was added and the reaction mixture was allowed to stir at −78° C. for 1 hour and was then allowed to warm to room temperature. The mixture was then poured into saturated ammonium chloride solution and extracted twice with ethyl acetate. The combined organic phases were washed with sodium thiosulphate solution, and with brine, before being dried and evaporated. The resultant foam was chromatographed using isohexane:diethyl ether (1:3) to give a foam which was recrystallised from diethyl ether/isohexane to give the sub-title compound as a pale yellow sold (350 mg).

Melting point: 140–142° C.

MS (APCI+ve) 488 (M+H)⁺

$^1$H NMR (CDCl$_3$) δ 0.85 (d, 6H), 2.09 (m, 1H), 3.41 (s, 3H), 3.53 (d, 2H), 5.65 (s, 2H), 6.51 (s, 1H), 6.85 (d, 1H), 7.42 (dd, 1H), 7.58 (m, 2H), 7.84–7.95 (m, 3H)

b) Trans-5-(2,3,4,6-Tetrahydro-3-methyl-1-(2-methylpropyl)-6-(1-naphthalenylmethyl)-2,4-dioxo-1H-pyrrolo[3,4-d]pyrimidin-5-yl)pent-3-enoic Acid 5-Iodo-3-methyl-1-(2-methylpropyl)-6-(1-naphthalenylmethyl)-1H-pyrrolo-[3,4-d]pyrimidine-2,4(3H,6H)-dione (100 mg), 4-pentenoic acid (0.042 ml), palladium acetate (5 mg) and tri(o-tolyl)phosphine (13 mg) were dissolved in triethylamine (1 ml) and acetonitrile (5 ml) and heated to 95° C. in a sealed pressure tube for 3 hours. The reaction mixture was allowed to cool to room temperature and was then evaporated to leave a residue which was chromatographed using ethyl acetate containing 1% acetic acid to give an oil (160 mg). Recrystallisation from diethyl ether/isohexane gave the title compound as a pale brown solid (48 mg).

Melting point: 176–180° C.

MS (APCI+ve) 460 (M+H)$^+$ (APCI–ve) 458 (M–H)$^-$ $^1$H NMR (CDCl$_3$) δ 0.89 (d, 6H), 2.14 (m, 1H), 2.98 (d, 2H), 3.40 (s, 3H), 3.56 (d, 2H), 3.82 (d, 2H), 5.50 (dt, [J=15 Hz, 6 Hz]1H), 5.57 (s, 2H), 5.65 (dt, [J=15 Hz, 7 Hz]1H), 6.17 (s, 1H), 6.69 (d, 1H), 7.39 (m, 1H), 7.55 (m, 2H), 7.80–7.93 (m, 3H)

EXAMPLE 13

5-(5-Hydroxypent-1-ynyl)-3-methyl-1-(2-methylpropyl)-6-(1-naphthalenylmethyl)-1H-pyrrolo[3,4-d]pyrimidine-2,4(3H,6H)-dione

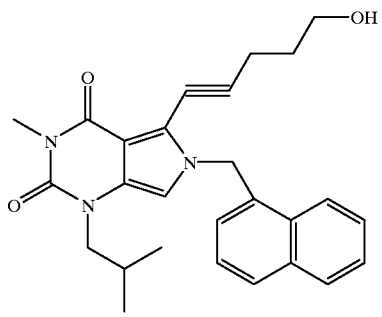

5-Iodo-3-methyl-1-(2-methylpropyl)-6-(1-naphthalenylmethyl)-1H-pyrrolo-[3,4-d]pyrimidine-2,4(3H,6H)-dione (100 mg), 4-pentyn-1-ol (0.080 ml), bis-triphenylphosphinepalladium (II) chloride (3 mg) and copper (I) iodide (1 mg) were dissolved in triethylamine (3 ml) and acetonitrile (1 ml) and heated to 90° C. in a sealed pressure tube for 3 hours. The reaction mixture was allowed to cool to room temperature and was then evaporated to leave a residue which was recrystallised from ethyl acetate. The resultant brown solid was chromatographed, eluting with ethyl acetate to give a white solid which was triturated with ethyl acetate to give the title compound (45 mg).

Melting point: 176–177° C.

MS (APCI+ve) 444 (M+H)$^+$ $^1$H NMR (CDCl$_3$) δ 0.84 (d, 6H), 1.82 (m, 2H), 2.08 (m, 1H), 2.36 (t, 1H), 2.65 (t, 2H), 3.40 (s, 3H), 3.50 (d, 2H), 3.77 (q, 2H), 5.67 (s, 2H), 6.10 (s, 1H), 7.08 (d, 1H), 7.47 (dd, 1H), 7.55 (m, 2H), 7.86–7.94 (m, 3H)

EXAMPLE 14

5-(5-Hydroxypentyl)-3-methyl-1-(2-methylpropyl)-6-(1-naphthalenylmethyl)-1H-pyrrolo[3,4-d]pyrimidine-2,4(3H,6H)-dione

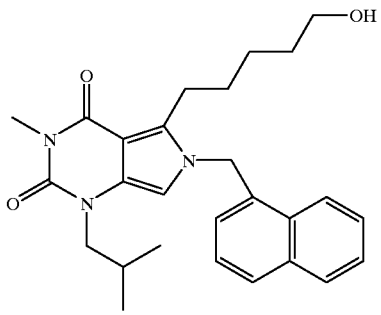

The compound of Example 13, 5-(5-hydroxypent-1-ynyl)-3-methyl-1-(2-methylpropyl)-6(1-naphthalenylmethyl)-1H-pyrrolo[3,4-d]pyrimidine-2,4(3H,6H)-dione (75 mg) was suspended in ethanol (50 ml). A suspension of 10% palladium on carbon (7 mg) in ethanol (3 ml) was added and the mixture was hydrogenated. When hydrogen uptake ceased, the reaction mixture was filtered and the solvent was removed by rotary evaporation. The crude product was purified by chromatography on silica eluting with ethyl acetate:isohexane (3:1) to give the title compound (29 mg) as an oil.

MS (APCI+ve) 448 (M+H)$^+$; (APCI–ve) 446 (M–H)$^-$ $^1$H NMR (CDCl$_3$) δ 0.90 (6H, d), 1.3–1.65 (6H, m), 2.17 (1H, m), 3.01 (2H, t), 3.41 (3H, s), 3.55–3.58 (4H, m), 3.64 (1H, t), 5.57 (2H, s), 6.70 (1H, d), 7.39 (1H, t), 7.56–7.60 (2H, m), 7.85–7.95 (3H, m)

EXAMPLE 15

5-(4-Hydroxybut-1-ynyl)-3-methyl-1-(2-methylpropyl)-6-(1-naphthalenylmethyl)-1H-pyrrolo[3,4-d]pyrimidine-2,4(3H,6H)-dione

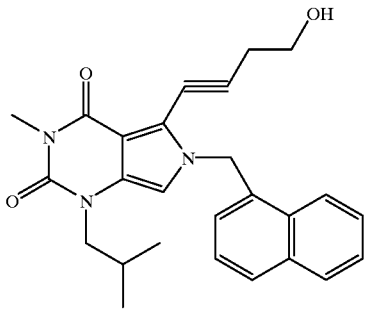

The title compound was prepared from 5-iodo-3-methyl-1(2-methylpropyl)-6-(1-naphthalenylmethyl)-1H-pyrrolo[3,4-d]pyrimidine-2,4(3H,6H)-dione and 3butyn-1-ol in a manner analogous to the method of Example 13 above.

Melting point: 170–171° C.

MS (APCI+ve)430 (M+H)$^+$ $^1$H NMR (CDCl$_3$)δ 0.84 (d, 6H), 2.09 (m, 1H), 2.74 (t, 2H), 3.40 (s, 3H), 3.50 (d, 2H), 3.88 (m, 3H), 5.68 (s, 2H), 6.08 (s, 1H), 7.10 (d, 1H), 7.46 (t, 1H), 7.55 (m, 2H), 7.87–7.94 (m, 3H)

EXAMPLE 16

5-(4-Hydroxybutyl)-3-methyl-1-(2-methylpropyl)-6-(1-naphthalenylmethyl)-1H-pyrrolo[3,4-d]pyrimidine-2,4(3H,6H)-dione

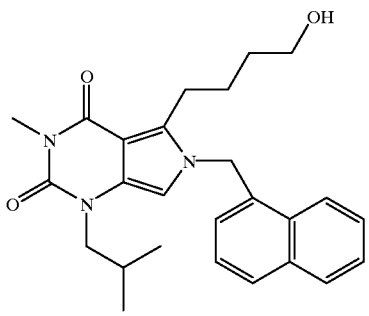

The title compound was prepared from the compound of Example 15, 5-(4-hydroxybut-1-ynyl)-3-methyl-1-(2-methylpropyl)-6-(1-naphthalenylmethyl)-1H-pyrrolo[3,4-d]pyrimidine-2,4(3H,6H)-dione, in a manner analogous to the method of Example 14 above.

MS (APCI+ve) 434 (M+H)$^+$; (APCI−ve) 432 (M−H)$^-$ $^1$H NMR (CDCl3)δ 0.88 (6H, d), 1.56–1.72 (4H, m), 2.18 (1H, m), 2.3 (1H,br), 3.01 (2H, t), 3.41 (3H, s), 3.57 (2H, d), 3.65–3.70 (2H, m), 5.58 (2H, s), 6.69 (1H, d), 7.41 (1H, t), 7.56–7.62 (2H, m), 7.84 (1H, d), 7.88–7.95 (2H, m)

EXAMPLE 17

5-(2,3,4,6-Tetrahydro-3-methyl-1-(2-methylpropyl)-6-(1-naphthalenylmethyl)-2,4-dioxo-1H-pyrrolo[3,4-d]pyrimidin-5-yl)pentanoic acid

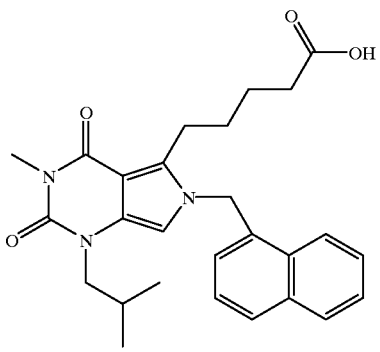

a) 5-(2,3,4,6-Tetrahydro-3-methyl-1-(2-methylpropyl)-6-(1-naphthalenylmethyl)-2,4-dioxo-1H-pyrrolo[3,4-d]pyrimidin-5yl)pent-4-ynoic acid The sub-title compound was prepared from 5-iodo-3-methyl-1-(2-methylpropyl)-6-(1naphthalenylmethyl)-1H-pyrrolo[3,4-d]pyrimidine-2,4(3H,6H)-dione, and 4-pentynoic acid in the presence of bistrimethylsilyltrifluoroacetamide in a manner analogous to the method of Example 13 above.

MS (APCI+ve) 458 (M+H)$^+$, (APCI−ve) 456 (M−H)$^-$ $^1$H NMR (CDCl$_3$) δ 0.85 (d, 6H), 2.07 (m, 1H), 2.61 (m, 2H), 2.80 (t, 2H), 3.39 (s, 3H), 3.48 (d, 2H), 5.65 (s, 2H), 6.09 (s, 1H), 7.11 (d, 1H), 7.44 (dd, 1H), 7.53 (m, 2H), 7.88–7.94 (m, 3H)

b) 5-(2,3,4,6-tetrahydro-3-methyl-1-(2-methylpropyl)-6-(1-naphthalenylmethyl)-2,4-dioxo-1H-pyrrolo[3,4-d]pyrimidin-5-yl)pentanoic acid The title compound was prepared from 5-(2,3,4,6-tetrahydro-3-methyl-1-(2-methylpropyl)-6-(1-naphthalenylmethyl)-2,4-dioxo-1H-pyrrolo[3,4-d]pyrimidin-5-yl)-pent-4-ynoic acid in a manner analogous to the method of Example 14 above.

Melting point: 146–147° C.

MS (APCI+ve) 462 (M+H), (APCI−ve) 460 (M−H)

$^1$H NMR (CDCl$_3$) δ 0.90 (d, 6H), 1.66 (m, 4H), 2.16 (m, 1H), 2.34 (t, 2H), 3.02 (t, 2H), 3.40 (s, 3.56 (d, 2H), 5.56 (s, 2H), 6.15 (s, 1H), 6.69 (d, 1H), 7.38 (t, 1H), 7.53–7.62 (m, 2H), 7.82–7.94 (m, 3H)

EXAMPLE 18

4-[(2,3,4,6-Tetrahydro-3-methyl-1-(2-methylpropyl)-6-(1-naphthalenylmethyl)-2,4-dioxo-1H-pyrrolo[3,4-d]pyrimidin-5-yl)thio]butanenitrile

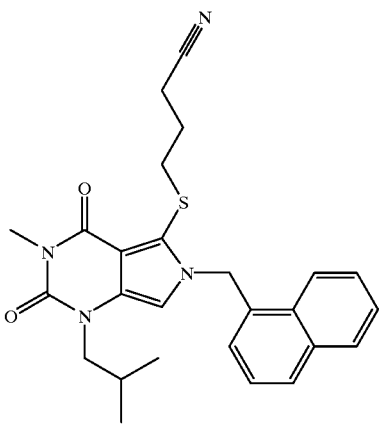

a) 5-[(3-{Methanesulphonyloxy}propyl)thio]-3-methyl-1-(2-methylpropyl)-6-(1-naphthalenylmethyl)-1H-pyrrolo[3,4-d]pyrimidine-2,4(3H, 6H)-dione 5-[(3-Hydroxypropyl)thio]-3-methyl-1-(2-methylpropyl)-6-(1-naphthalenylmethyl)-1H-pyrrolo[3,4-d]pyrimidine-2,4(3H,6H)-dione (J. Med. Chem., 1995, 38, 2557) (260 mg), methanesulphonyl chloride (54 μl) and triethylamine (97 μl) were dissolved in dichloromethane (15 ml) and the mixture was stirred overnight. The reaction mixture was poured onto sodium bicarbonate (aqueous) and extracted twice with ethyl acetate. The extracts were combined, dried, filtered and evaporated to give the subtitle compound as a gum (391 mg).

MS (+ve APCI) (M+H)$^+$ 530 b) 4-[(2,3,4,6-Tetrahydro-3-methyl-1-(2-methylpropyl)-6-(1-naphthalenylmethyl)-2,4-dioxo-1H-pyrrolo[3,4-d]pyrimidin-5-yl)thio]butanenitrile 5-[(3-{Methanesulphonyloxy}propyl)thio]-3-methyl-1-(2-methylpropyl)-6-(1-naphthalenylmethyl)-1H-pyrrolo[3,4-d]pyrimidine-2,4(3H,6H)-dione (391 mg) was dissolved in dimethyformamide (15 ml) and sodium cyanide (254 mg) was added. The mixture was sonicated for 4 hours and then poured onto sodium bicarbonate (aqueous). The mixture was extracted thrice with ethyl acetate, the extracts were combined, washed twice with water and once with brine, then dried, filtered and evaporated. The resultant oil was chromatographed, eluting with ethyl acetate: isohexane (4:5) and then triturated with cyclohexane-ethyl acetate to give the title compound (95 mg).

Melting point: 127–128° C.

MS (+ve APCI) (M+H)$^+$ 461

$^1$H MNR (CDCl$_3$) δ 0.89 (6H, d), 1.86 (2H, quin), 2.07–2.19 (1H, m), 2.48 (2H, t), 3.02 (2H, t), 3.42 (3H, s), 3.57 (2H, d), 5.85 (2H, s), 6.42 (1H, s), 6.77 (1H, d), 7.37 (1H, t), 7.56–7.63 (2H, m), 7.85 (1H, d), 7.91–7.95 (2H, m)

EXAMPLE 19

5-[(3-{1H-Tetrazol-5-yl}propyl)thio]-3-methyl-1-(2-methylpropyl)-6-(1-naphthalenylmethyl)-1H-pyrrolo[3,4-d]pyrimidine-2,4(3H,6H)-dione

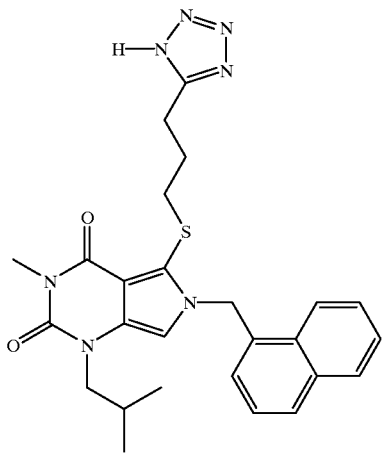

The compound of Example 18, 4-[(2,3,4,6-tetrahydro-3-methyl-1-(2-methylpropyl)-6-(1naphthalenylmethyl)-2,4-dioxo-1H-pyrrolo[3,4-d]pyrimidin-5-yl)thio]butanenitrile (98 mg) was dissolved in toluene (20 ml) and trimethyltin azide (100 mg) was added. The solution was heated under reflux for 110 hours, then the solvent was evaporated and the residue was chromatographed, eluting with ethanol: dichloromethane (1:19), to give the title compound (30 mg).

MS (+ve APCI) (M+H)$^+$ 504

$^1$H NMR (DMSO d-6) δ 0.86 (6H, d), 1.79 (2H, quin), 2.05–2.16 (1H, m), 2.87 (2H, t), 2.91 (2H, t), 3.23 (3H, s), 3.59 (2H, d), 5.90 (2H, s), 6.54 (1H, d), 7.19 (1H, s), 7.38 (1H, t), 7.57–7.66 (2H, m), 7.85 (1H, d), 7.99 (1H, d), 8.17 (1H, d)

EXAMPLE 20

3-Methyl-1-(2-methylpropyl)-6-(1-naphthalenylmethyl)-5-[(2-pyridinyl)thio]-1H-pyrrolo[3,4-d]pyrimidine-2,4(3H,6H)-dione

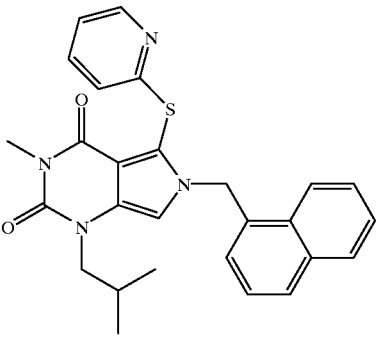

Prepared from 3-methyl-1-(2-methylpropyl)-6-(1-naphthalenylmethyl)-1H-pyrrolo-[3,4-d]pyrimidine-2,4(3H, 6H)-dione (J. Med. Chem., 1995, 38, 2557) and 2,2'-pyridyl disulphide following the method of Example 7.

Melting point: 146–148° C.

MS (FAB) ((M+H)$^+$) 471

$^1$H NMR (CDCl$_3$) δ 0.85 (6H, d), 2.08 (1H, m), 3.38 (3H, s), 3.52 (2H, d), 5.78 (2H, s), 6.39 (1H, s), 7.03 (1H, m), 7.10 (2H, m), 7.44 (4H, m), 7.86 (3H, m), 8.38 (1H, d)

EXAMPLE 21

3-Methyl-1-(2-methylpropyl)-6-(1-naphthalenylmethyl)-5-[(2-pyridinyl)sulphinyl]-1H-pyrrolo[3,4-d]pyrimidine-2,4(3H,6H)-dione

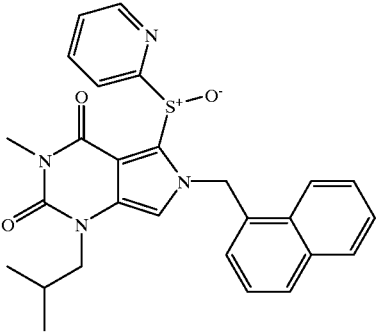

Prepared from the compound of Example 20, 3-methyl-1-(2-methylpropyl)-6-(1-naphthalenylmethyl)-5-[(2-pyridinyl)thio]-1H-pyrrolo[3,4-d]pyrimidine-2,4(3H,6H)-dione and potassium peroxymonosulphate (commercially sold under the trade mark "OXONE") following the method of Example 8c).

MS (FAB) ((M+H)$^+$) 487

$^1$H NMR (CDCl$_3$) δ 0.81 (6H, d), 2.04 (1H, m), 3.43 (3H, s), 3.49 (2H, m), 5.83 (1H, d), 5.94 (1H, d), 6.64 (1H, d), 7.07 (1H, m), 7.20 (1H, t), 7.47 (3H, m), 7.70 (2H, m), 7.84 (1H, d), 7.92 (1H, d), 8.48 (1H, d)

EXAMPLE 22

3-Methyl-1-(2-methylpropyl)-6-(1-naphthalenylmethyl)-5-[(4-pyridinyl)thiol]-1H-pyrrolo[3,4-d]pyrimidine-2,4(3H,6H)-dione

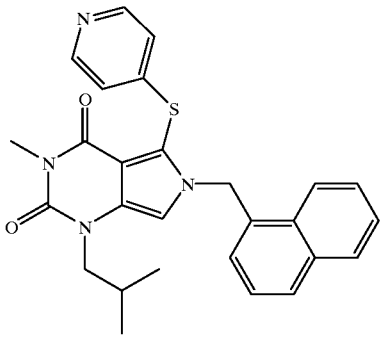

Prepared from 3-methyl-1-(2-methylpropyl)-6(1-naphthalenylmethyl)-1Hpyrrolo-[3,4-d]pyrimidine-2,4(3H,6H)-dione (J. Med. Chem., 1995, 38, 2557) and 4,4'-pyridyl disulphide following the method of Example 7.

Melting point: 154–156° C.

MS (FAB) 471 ((M+H)$^+$)

$^1$H NMR (CDCl$_3$) δ 0.87 (6H, d), 2.11 (1H, m), 3.38 (3H, s), 3.56 (2H, d), 5.70 (2H, s), 6.51 (1H, s), 6.88 (2H, m), 6.92 (1H, d), 7.35 (1H, t), 7.48 (2H, m), 7.75 (1H, d) 7.81 (1H, d), 7.87 (1H, d), 8.34 (2H,d)

EXAMPLE 23

5-([3-Methoxyphenyl]thio)-3-methyl-1-(2-methylpropyl)-6-(1-naphthalenylmethyl)-1H-pyrrolo[3,4-d]pyrimidine-2,4(3H,6H)-dione

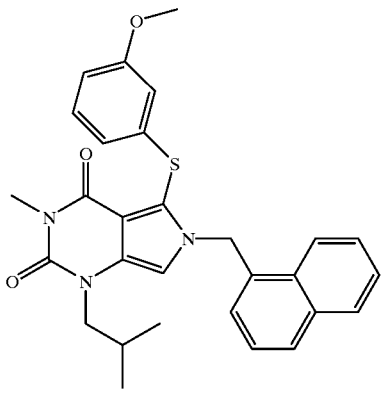

a) 3-Methoxyphenyldisulphide

4-Toluenesulphonylchloride (8 g) was added portionwise to a solution of 3-methoxythiophenol (5ml) and triethylamine (5.6 ml) in dichloromethane (50 ml) at 0° C. After 3.5 hours the reaction mixture was diluted with dichloromethane and washed once with water, twice with dilute hydrochloric acid, twice with saturated sodium hydrogen carbonate solution and once with brine. The organic layer was dried over magnesium sulphate, filtered and evaporated in vacuo. Purification of the residue by chromatography on silica gel, eluting with isohexane/ethyl acetate (19:1), gave the subtitle compound as an oil (2.65 g).

MS (EI) (M$^+$)278

$^1$H NMR (CDCl$_3$) δ 3.77 (6H, s), 6.75 (2H, dd), 7.06 (2H, s), 7.07 (2H, d), 7.21 (2H, t)

b) 5-([3-Methoxyphenyl]thio)-3-methyl-1-(2-methylpropyl)-6-(1-naphthalenylmethyl)-1H-pyrrolo[3,4-d]pyrimidine-2,4(3H,6H)-dione To a stirred solution of 3-methyl-1-(2-methylpropyl)-6-(1-naphthalenylmethyl)-1H-pyrrolo[3,4-d]pyrimidine-2,4 (3H,6H)-dione (0.50 g) (J. Med. Chem., 1995, 38, 2557) and 3-methoxyphenyldisulphide(0.77 g) in anhydros tetrahydrofuran (20 ml) at −70° C. was added dropwise a solution of lithium diisopropylamide (2.79 mmol) in tetrahydrofuran (7 ml). The solution was stirred for a further 2 hours at −70° C. and then allowed to warm to ambient temperature. Water (10 ml) was added and the solution was extracted with ethyl acetate. The organic phase was separated and washed once with water, twice with dilute hydrochloric acid, twice with saturated sodium hydrogen carbonate solution and once with brine. The organic layer was dried over magnesium sulphate and evaporated in vacuo. Purification by chromatography on silica gel, eluting with isohexane/ethyl acetate (4:1 to 2:1) followed by recrystallisation from isohexane/ethyl acetate (4:1), gave the title compound (430 mg).

Melting point: 130–133° C.

MS (APCI) 500 ((M+H)$^+$)

$^1$H NMR (DMSO) δ 0.86 (6H, d), 2.1–2.2 (1H, m), 3.22 (3H, s), 3.60 (3H, s), 3.62 (2H, d), 5.86 (2H, s), 6.55–6.65 (3H, m), 6.73 (1H, dd), 7.16 (1H, t), 7.33 (2H, t), 7.50–7.60 (2H, m), 7.83 (1H, d), 7.96 (1H, dd), 8.05 (1H, dd)

EXAMPLE 24

5-([3-Hydroxyphenyl]thio)-3-methyl-1-(2-methylpropyl)-6-(1-naphthalenylmethyl)-1H-pyrrolo[3,4-d]pyrimidine-2,4(3H,6H)-dione

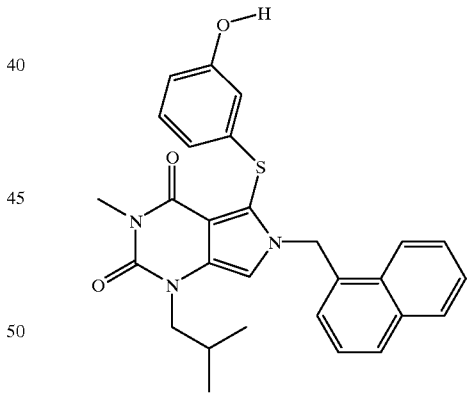

A solution of boron tribromide in dichloromethane (1M, 3 ml) was added to a solution of 5-([3-methoxyphenyl]thio)-3-methyl-1-(2-methylpropyl)-6-(1-naphthalenylmethyl)-1H-pyrrolo[3,4-d]pyrimidine-2,4(3H,6H)-dione (200 mg) (compound of Example 23) in dichloromethane (20 ml) at ambient temperature. After 6 hours, water (10 ml) was added carefully and the reaction mixture was partitioned between dichloromethane and brine. The organic phase was dried over magnesium sulphate, filtered and evaporated in vacuo. Purification by chromatography on silica gel, eluting with isohexane/ethyl acetate (2:1 to 1:1) followed by recrystallisation from isohexane/ethyl acetate (3:1), gave the title compound (120 mg).

Melting point: 150–151° C.

MS (APCI) 486 ((M+H)+)

1H NMR (DMSO) δ 0.86 (6H, d), 2.1–2.2 (1H, m), 3.23 (3H, s), 3.61 (2H, d), 5.83 (2H, s), 6.45 (1H, t), 6.53 (2H, dt), 6.63 (1H, d), 7.03 (1H, t), 7.30 (1H, s), 7.36 (1H, t), 7.50–7.60 (2H, m), 7.85 (1H, d), 7.96 (1H, dd), 8.05 (1H, dd), 9.51 (1H, brs)

EXAMPLE 25

5-([4-Methoxyphenyl]thio)-3-methyl-1-(2-methylpropyl)-6-(1-naphthalenylmethyl)-1H-pyrrolo[3,4-d]pyrimidine-2,4(3H,6H)-dione

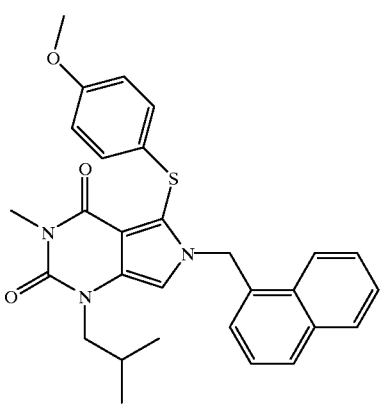

Prepared from 3-methyl-1-(2-methylpropyl)-6-(1-naphthalenylmethyl)-1H-pyrrolo[3,4-d]pyrimidine-2,4(3H,6H)-dione (0.50 g) (J. Med. Chem., 1995, 38, 2557) and 4-methoxyphenyldisulphide following the method of Example 23.

Melting point: 60–63° C.

MS (APCI) 500 ((M+H)+)

1H NMR (DMSO) δ 0.81 (6H, d), 2.1–2.2 (1H, m), 3.24 (3H, s), 3.58 (2H, d), 3.68 (3H, s), 5.91 (2H, s), 6.50 (1H, d), 6.80 (2H, d), 7.20 (3H, d), 7.31 (1H, t), 7.55–7.60 (2H, m), 7.83 (1H, d), 7.98 (1H, dd), 8.08 (1H, dd)

EXAMPLE 26

5-([4-Hydroxyphenyl]thio)-3-methyl-1-(2-methylpropyl)-6-(1-naphthalenylmethyl)-1H-pyrrolo[3,4-d]pyrimidine-2,4(3H,6H)-dione

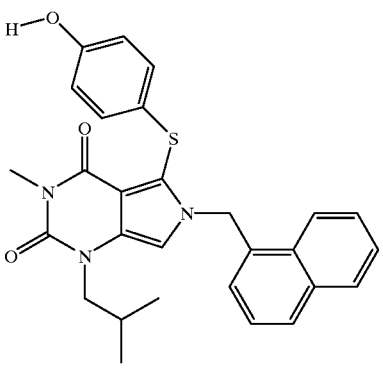

Prepared from the compound of Example 25 following the method of Example 24.

Melting point: 228–230° C.

MS (APCI) 486 ((M+H)+)

1H NMR (DMSO) δ 0.83 (6H, d), 2.1–2.2 (1H, m), 3.24 (3H, s), 3.56 (2H, d), 5.91 (2H, s), 6.52 (1H, s), 6.63 (2H, d), 7.14–7.16 (3H, m), 7.35 (1H, t), 7.55–7.60 (2H, m), 7.84 (1H, d), 7.97 (1H, dd), 8.06 (1H, dd), 9.59 (1H, s)

EXAMPLE 27

5-([2-Methoxyphenyl]thio)-3-methyl-1-(2-methylpropyl)-6-(1-naphthalenylmethyl)-1H-pyrrolo[3,4-d]pyrimidine-2,4(3H,6H)-dione

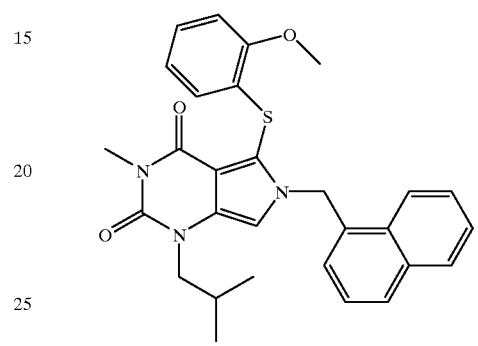

Prepared following the method of Example 23 using 3-methyl-1-(2-methylpropyl)-6-(1-naphthalenylmethyl)-1H-pyrrolo[3,4-d]pyrimidine-2,4(3H,6H)-dione (0.50 g) (J. Med. Chem., 1995, 38, 2557) and 2-methoxyphenyldisulphide.

Melting point: 153° C.

MS (APCI) 500 ((M+H)+)

1H NMR (DMSO) δ 0.87 (6H, d), 2.1–2.2 (1H, m), 3.21 (3H, s), 3.61 (2H, d), 3.69 (3H, s), 5.85 (2H, s), 6.59 (1H, d), 6.69 (1H, dd), 6.81 (1H, dt), 6.91 (1H, dd), 7.12 (1H, dt), 7.34 (2H, t), 7.55–7.60 (2H, m), 7.82 (1H, d), 7.96 (1H, dd), 8.06 (1H, dd)

EXAMPLE 28

5-([2-Hydroxyphenyl]thio)-3-methyl-1-(2-methylpropyl)-6-(1-naphthalenylmethyl)-1H-pyrrolo[3,4-d]pyrimidine-2,4(3H,6H)-dione

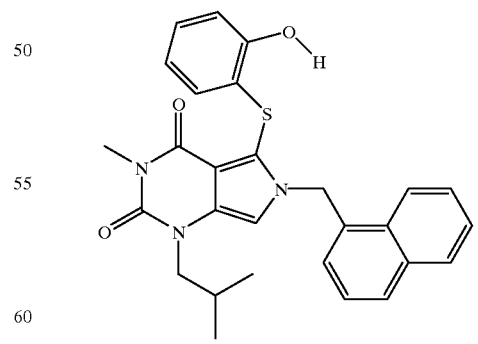

Prepared from the compound of Example 27 following the method of Example 24.

Melting point: 190–192° C.

MS (APCI) 486 ((M+H)+)

$^1$H NMR (DMSO) δ 0.85 (6H, d), 2.1–2.2 (1H, m), 3.22 (3H, s), 3.59 (2H, d), 5.88 (2H, s), 6.63 (1H, d), 6.69 (1H, dd), 6.69 (2H, dt), 7.00 (1H, dt), 7.26 (1H, s), 7.37 (1H, t), 7.55–7.60 (2H, m), 7.85 (1H, d), 7.96 (1H, dd), 8.05 (1H, dd), 10.02 (1H, s)

EXAMPLE 29

Inhibition of Human Mixed Lymphocyte Reaction (MLR)

The MLR test was performed in 96-well flat bottomed microtitre plates. Compounds were prepared as 10 mM stock solution in dimthyl sulphoxide. A 50 fold dilution of this was prepared in a cell culture solution obtained from the Roswell Park Memorial Institute (RPMI 1640 medium). Serial dilutions were prepared from this solution. 10 μl of the 50 fold diluted stock, or dilutions of it, were added to the wells to give concentrations in the assay starting at 9.5 μm and decreasing. Into each well was placed $1.5 \times 10^5$ cells from each of two responding donors in a final volume of 0.2 ml RPMI 1640 medium supplemented with 10% human serum, 2 mM L-glutamine and penicillin/streptomycin. The cells were incubated at 37° C. in a humidified atmosphere at 5% carbon dioxide for 120 hours. $^3$H-Thymidine (0–5 μCi) was added for the final 6 hours of the incubation. The level of radioactivity incorporated by the cells was then determined, which is a measure of T-cell proliferation.

The title compounds of Examples 1 to 28 were found to exhibit an $IA_{50}$ value of less than $1 \times 10^{-6}$ M in the above test.

What is claimed is:

1. A process for the preparation of a compound of formula (I)

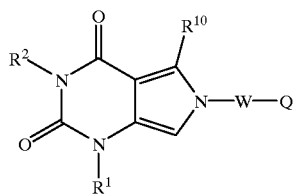

(I)

wherein

W represents —CH$_2$—or a bond; Q represents Ar$^1$ or Ar$^2$; in the case where W represents —CH$_2$—, Q represents an aryl group Ar$^1$ where Ar$^1$ represents naphthyl, phenyl, quinolyl, isoquinolyl, indolyl, benzofuranyl or benzothienyl; in the case where W represents a bond, Q represents an aryl group A$^2$ wherein Ar$^2$ represents acenaphthenyl, fluorenyl or indanyl; wherein the ring systems which Ar$^1$ and Ar$^2$ represent may all be optionally substituted by one or more substituents selected from C$_{1-4}$ alkyl, C$_{1-4}$ alkoxy, halogen, or trifluoromethyl; R$^{10}$ represents X—(A)$_p$—Y; X represents S(O)$_n$, C≡C, (CH$_2$)$_2$, CH=CH or CH$_2$CH=CH; n represents 0, 1 or 2; A represents C$_{1-6}$ alkylene; p is 0 or 1; Y represents CN, OR$^{11}$, CO$_2$R$^{12}$, CONR$^{13}$R$^{14}$, NR$^{15}$R$^{16}$, NHSO$_2$R$^{17}$, NHCOR$^{18}$ or an optionally substituted aryl or heteroaryl group, provided that when X represents S(OP)$_n$, and Y is other than an optionally substituted aryl or heteroaryl group, then p is 1 and also provided that when X represents S(O)$_n$, p is 1 and Y represents OH, then n is not 0; R$^{13}$ and R$^{14}$ independently represent H, C$_{1-5}$ alkyl or phenyl, which latter group may be substituted by one or more substituents selected from C$_{1-4}$ alkyl, C$_{1-4}$ alkoxy, halogen, or CO$_2$R$^{21}$; and R$^1$, R$^2$, R$^{11}$, R$^{12}$, R$^{15}$, R$^{16}$, R$^{17}$, R$^{18}$ and R$^{21}$ independently represent H or C$_{1-5}$ alkyl; or a pharmaceutically acceptable derivative thereof, which process comprises, when X represents S, A represents a C$_{1-6}$ alkylene group, Y represents CO$_2$R$^{12}$ and R$^{12}$ represents C$_{1-5}$ alkyl, reacting a compound of the formula (VI)

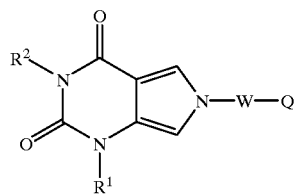

(VI)

in which R$^1$, R$^2$, W and Q are as defined above, with a compound of formula

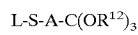

L-S-A-C(OR$^{12}$)$_3$     (VII)

wherein L is a leaving group and A and R$^{12}$ are as defined above, followed by hydrolysis of the resulting ortho ester.

* * * * *